(12) United States Patent
Cole et al.

(10) Patent No.: US 10,478,171 B1
(45) Date of Patent: Nov. 19, 2019

(54) FLUSH ANCHOR METHOD AND APPARATUS

(71) Applicant: Little Engine, LLC, Belmont, NC (US)

(72) Inventors: J. Dean Cole, Orlando, FL (US); Franz W. Kellar, Gastonia, NC (US); Michael D. Bissette, Belmont, NC (US); Harold L. Crowder, Concord, NC (US); Mark S. Wabalas, Huntersville, NC (US)

(73) Assignee: LITTLE ENGINE, LLC, Belmont, NC (US)

( * ) Notice: Subject to any disclaimer, the term of this patent is extended or adjusted under 35 U.S.C. 154(b) by 0 days.

(21) Appl. No.: 16/192,300

(22) Filed: Nov. 15, 2018

Related U.S. Application Data

(60) Provisional application No. 62/718,730, filed on Aug. 14, 2018.

(51) Int. Cl.
*A61B 17/04* (2006.01)

(52) U.S. Cl.
CPC .. *A61B 17/0401* (2013.01); *A61B 2017/0424* (2013.01); *A61B 2017/0427* (2013.01); *A61B 2017/0453* (2013.01)

(58) Field of Classification Search
CPC ........ A61B 17/0401; A61B 2017/0404; A61B 2017/0409; A61B 2017/0414; A61B 2017/0422; A61B 2017/0424; A61B 2017/0438; A61B 2017/044; A61B 2017/0445; A61B 2017/0446; A61B 2017/0448; A61B 2017/045; A61B 2017/0451; A61B 2017/0458
See application file for complete search history.

(56) References Cited

U.S. PATENT DOCUMENTS

| | | | |
|---|---|---|---|
| 2001/0008971 A1* | 7/2001 | Schwartz | A61B 17/0401 606/232 |
| 2003/0032983 A1* | 2/2003 | Bonutti | A61B 17/0487 606/232 |
| 2005/0222488 A1* | 10/2005 | Chang | A61B 17/00234 600/37 |
| 2008/0288060 A1* | 11/2008 | Kaye | A61B 17/0401 623/2.36 |
| 2014/0194907 A1* | 7/2014 | Bonutti | A61B 17/8866 606/151 |

* cited by examiner

*Primary Examiner* — Ryan J. Severson
*Assistant Examiner* — Christian D Knauss
(74) *Attorney, Agent, or Firm* — Trego, Hines & Ladenheim, PLLC

(57) ABSTRACT

An apparatus for anchoring a tensile member to bone includes a housing with first and second ends and a hollow interior space. A collet is disposed in the interior space, the collet defining a central bore for accepting a tensile member therethrough, and an exterior surface. A sleeve has opposed interior and exterior surfaces and is disposed in the interior space axially adjacent to the collet, and is movable axially between first and second positions. At least one of the exterior surface of the collet and the interior surface of the sleeve is tapered and the sleeve and the collet are arranged such that movement of the sleeve from the first position to the second position will cause the interior surface of the sleeve to bear against the exterior surface of the collet, causing the collet to swage radially inwards around and against the tensile member, without moving axially.

23 Claims, 28 Drawing Sheets

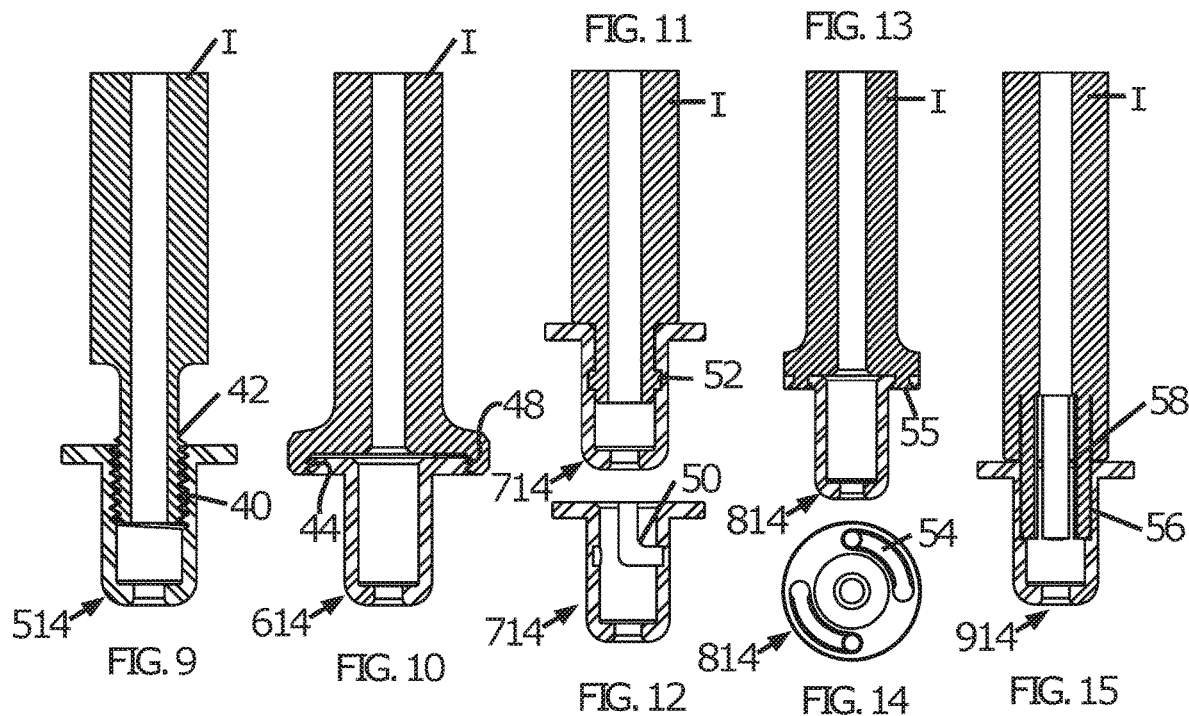

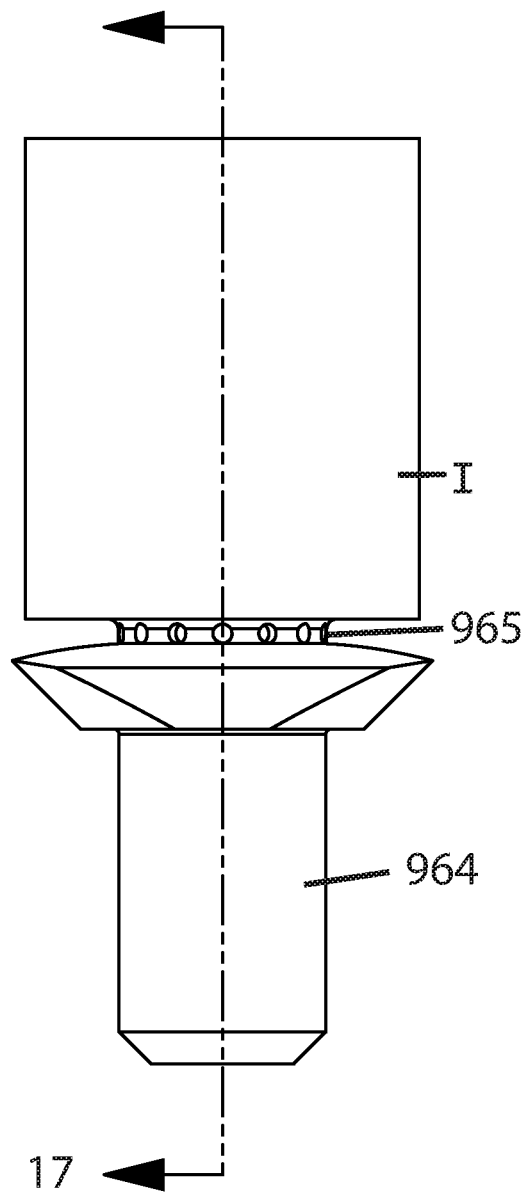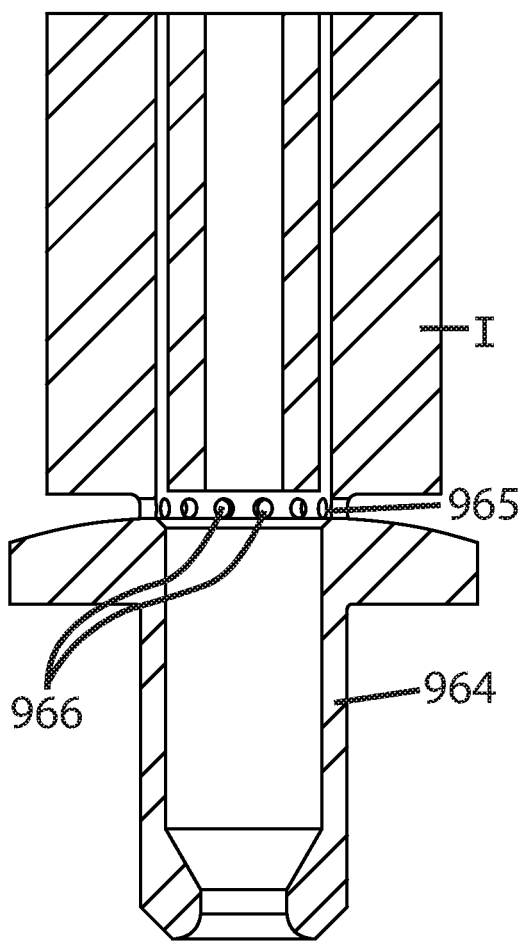
FIG. 16
FIG. 17

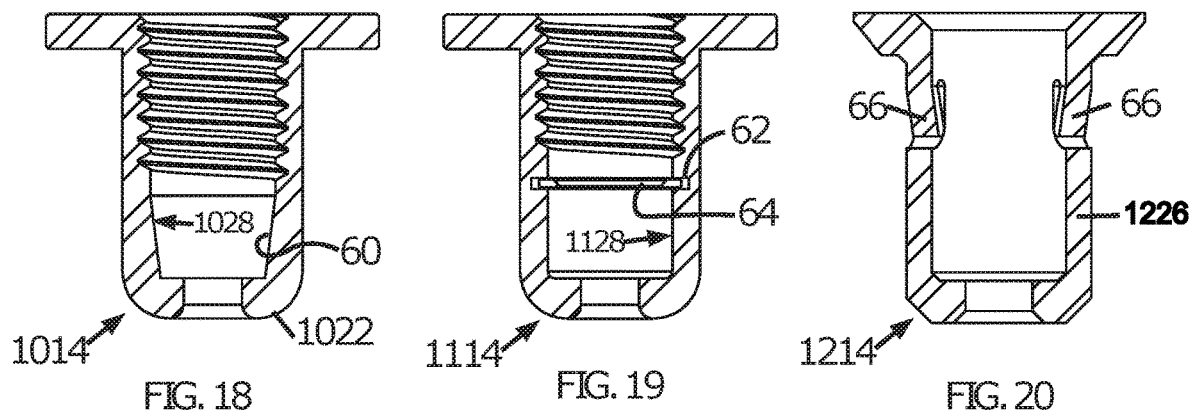

FIG. 21
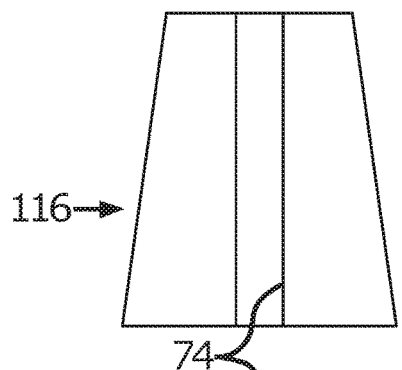
FIG. 23
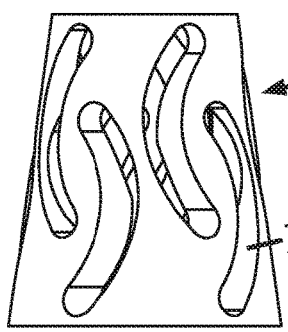
FIG. 25
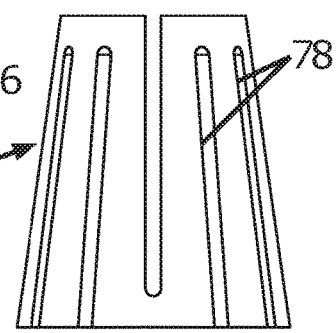
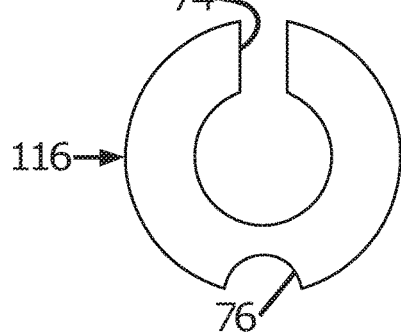
FIG. 22
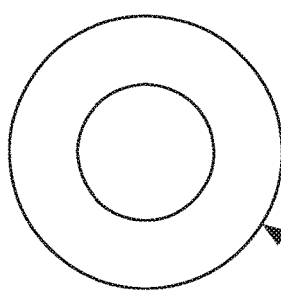
FIG. 24
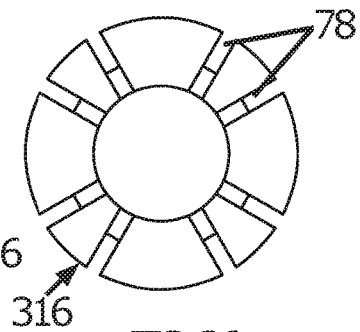
FIG. 26

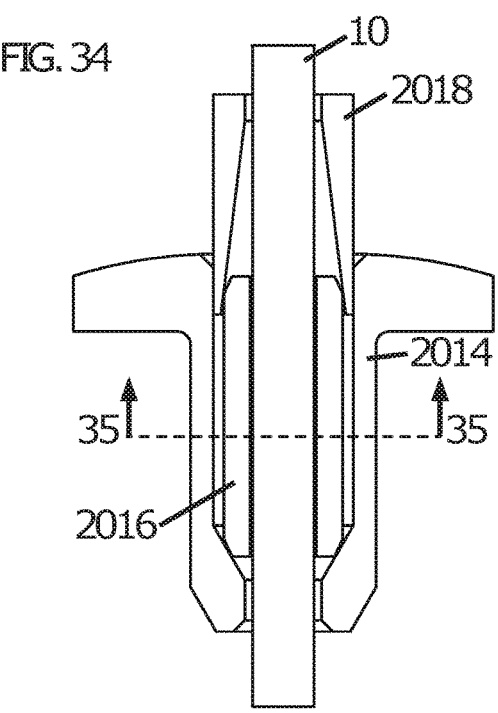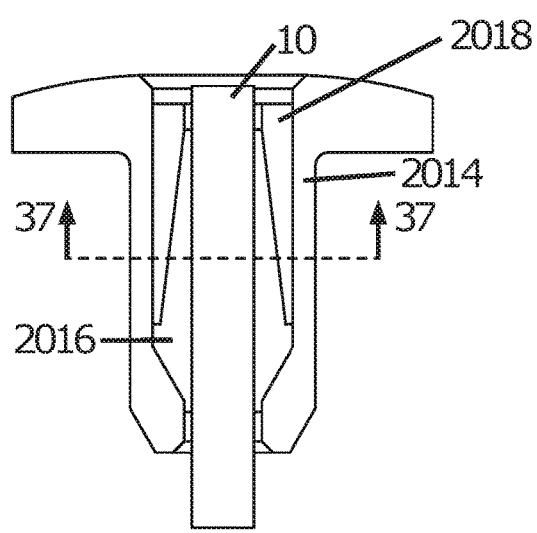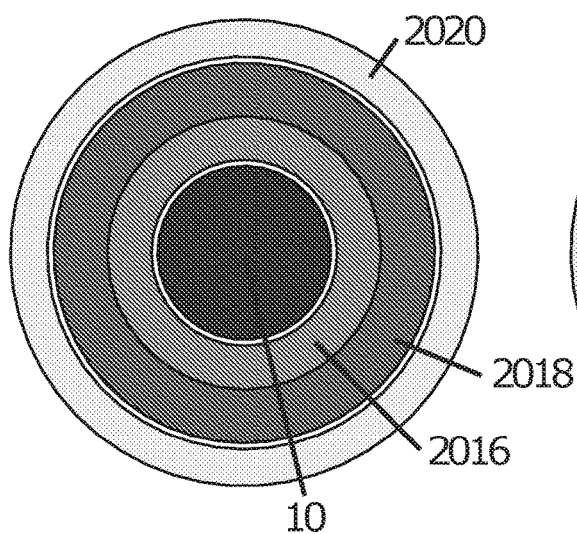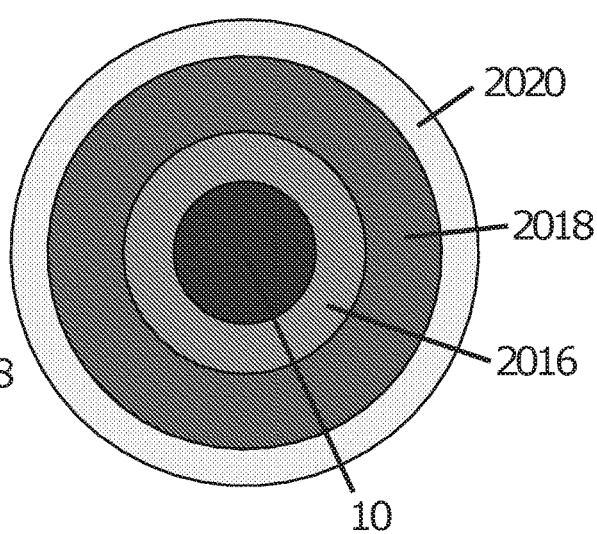

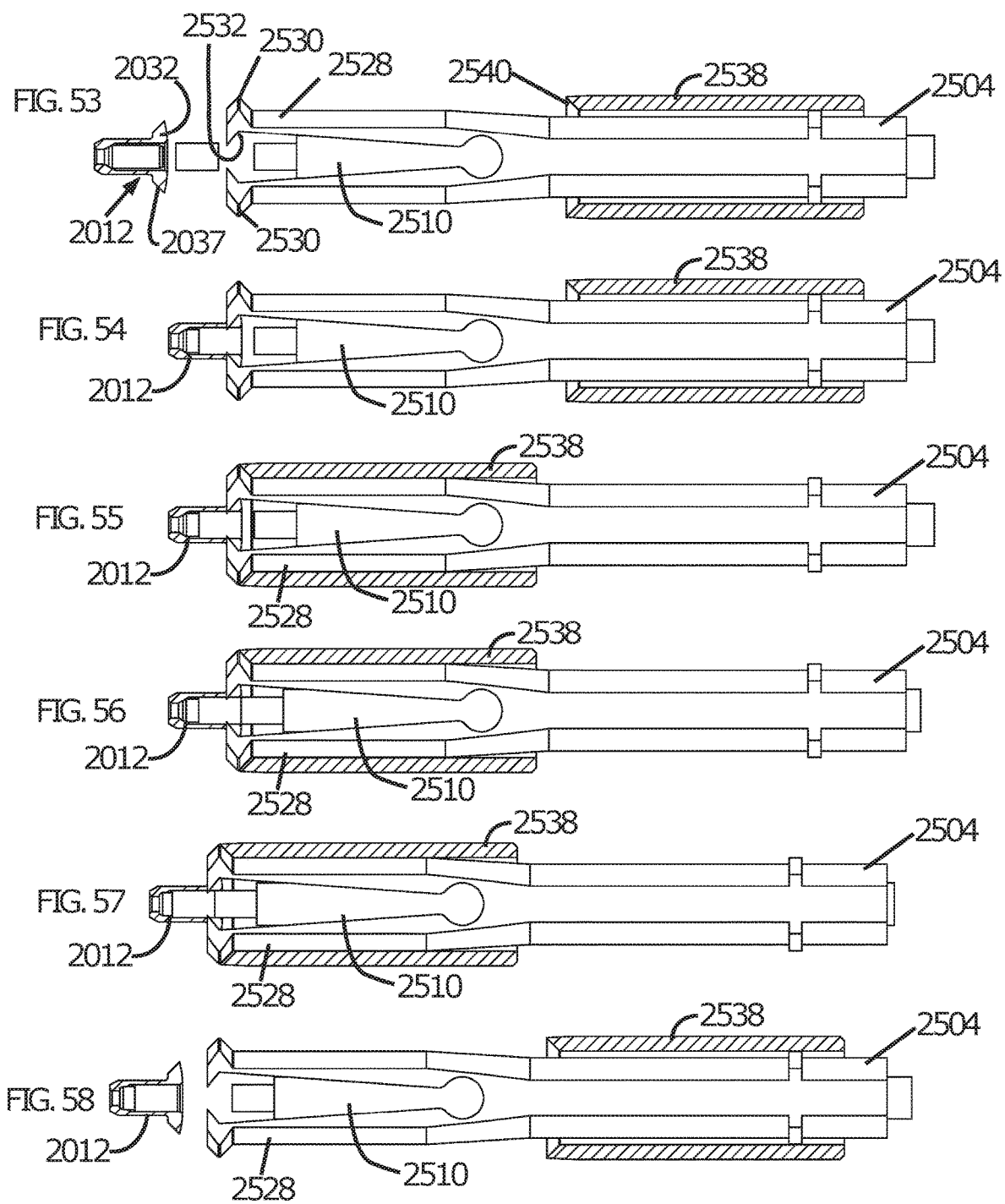

FLUSH ANCHOR METHOD AND APPARATUS

BACKGROUND OF THE INVENTION

This invention relates generally to medical implants, and more particularly to apparatus for applying tension along or across a ligament to repair, augment, or replace it, or applying tension across a bone fracture to reduce it.

Medical implants for tensioning purposes typically comprise one or more tensile members (e.g., sutures or orthopedic cables) connected to one or more anchors (e.g., suture anchors or suture locks) to create a converging tensile force between the two anchors. This general concept has been used in the orthopedic and sports medicine fields to repair torn or damaged tendons and ligaments, to replace missing or displaced tendons and ligaments, and to anchor grafted or artificial tendons and ligaments to bones so that they can grow back together.

Prior art anchor/tensile member configurations typically fall into three functional categories; (1) a configuration in which the tensile member in held in place by an interference fit between the tensile member and bone, (2) a configuration in which the tensile member is tied, glued, melted, or otherwise connected to the anchor during manufacturing or intraoperatively, and (3) a configuration in which the tensile member is tensioned or made tight with the use of one of many available and well-known slip-knots.

It is often desirable to have the ability to tension the configuration provisionally (i.e. without setting a final irreversible tension) so that the effect of a particular level of tension can be evaluated and have the opportunity to "settle in" before it is made permanent.

However, one problem with prior art anchors is that they do not generally permit accurate provisional tensioning. When standard suture anchors are used, the tension is set by estimating the length of the final suture implant or tying a slipknot that can be tightened by hand. Some are even tensioned by wrapping the suture around a Kirschner wire ("K-wire") and twisting the wire to tighten. Even if the initial tension is estimated well, suture will settle into the soft tissue around it and lose tension after implantation. There does not currently exist a good way to tension a suture to a known load, "trial" its tension and allow for some settle in, re-tension, and repeat as needed.

Another problem with prior art suture tensioning techniques is that of determining that excessive tension is applied. More specifically, because the tension in a suture strand does not exceed its failure load during the operative procedure does not mean it will not experience a load greater than its failure load during cyclic loading in-situ.

BRIEF SUMMARY OF THE INVENTION

At least one of these problems is addressed by a modular orthopedic device, and implant/instrument system that includes a bone anchor device that is used to secure a tensile member under tension.

According to one aspect of the technology described herein, an apparatus is provided for anchoring a tensile member to bone, including: an anchor, including: a housing extending along a central axis between open first and second ends, and having a hollow interior; a collet disposed in the hollow interior of the housing, the collet having a peripheral wall defining a central bore for accepting a tensile member therethrough and an exterior surface, wherein the collet is configured to be swaged around and against the tensile member; a sleeve having a peripheral wall defining opposed interior and exterior surfaces, the sleeve disposed in the hollow interior of the housing and positioned generally axially adjacent to the collet, so as to be movable parallel to the central axis between first and second positions; and wherein at least one of the exterior surface of the collet and the interior surface of the sleeve is tapered and the sleeve and the collet are arranged such that movement of the sleeve from the first position to the second position will cause the exterior interior surface of the sleeve to bear against the exterior surface of the collet, causing the collet to swage radially inwards around and against the tensile member without moving axially relative to the housing or tensile member.

BRIEF DESCRIPTION OF THE DRAWINGS

The invention may be best understood by reference to the following description taken in conjunction with the accompanying drawing figures in which:

FIG. 9 is a schematic cross-sectional view of a housing having female threads engaging an instrument having male threads;

FIG. 10 is a schematic cross-sectional view of a housing having male threads engaging an instrument having female threads;

FIGS. 11 and 12 are schematic cross-sectional views of a housing having bayonet fitting slots engaging bayonet lugs of a corresponding instrument;

FIGS. 13 and 14 are schematic cross-sectional and top plan views, respectively of a housing having a circumferential slot engaging axial lugs of a corresponding instrument;

FIG. 15 is a schematic cross-sectional view of a housing having a counterbore formed therein engaging collet jaws of a corresponding instrument;

FIGS. 16 and 17 are schematic side elevation and cross-sectional views, respectively of a housing having a breakaway connection to a corresponding instrument;

FIG. 18 is a schematic cross-sectional view of a housing having a tapered sleeve retention feature;

FIG. 19 is a schematic cross-sectional view of a housing having a snap ring sleeve retention feature;

FIG. 20 is a schematic cross-sectional view of a housing having resilient sleeve retention tabs;

FIGS. 21 and 22 are schematic cross-sectional and end views, respectively, of a collet having a slotted construction;

FIGS. 23 and 24 are schematic cross-sectional and end views, respectively, of a collet having curvilinear slots formed therein;

FIGS. 25 and 26 are schematic cross-sectional and end views, respectively, of a collet having a spring structure

FIG. 34 is a cross-sectional view of the anchor FIG. 30 in an assembled condition, before compression;

FIG. 35 is a sectional view taken along lines 35-35 of FIG. 34;

FIG. 36 is a cross-sectional view of the anchor FIG. 30 in a compressed condition;

FIG. 37 is a sectional view taken along lines 37-37 of FIG. 36;

FIG. 53 is a schematic cross-sectional view of a distal end of a stem of an alternative installation instrument of, showing an anchor ready to be loaded therein;

FIG. 54 is a view of the stem of FIG. 53, showing an anchor lightly received in jaws of the stem, with a locking sleeve retracted;

FIG. 55 is another view of the stem of FIG. 53, showing a locking sleeve pushed down over the jaws to secure the anchor;

FIGS. 56 and 57 are sequential views showing actuation of a pushrod of the stem of FIG. 49;

FIG. 58 is another view of the stem of FIG. 49, showing a clip in a released position, with the jaws opened to release the anchor;

DETAILED DESCRIPTION OF THE INVENTION

In general, the technology described herein provides a modular device and implant system and method that enables provisional and permanently stable tensioning of the tensile member, with minimally-invasive access to and limited visualization of the bone surface, using a device that is small and low-profile to prevent stress-shielding and soft tissue hang-up, implanted by simple and intuitive instrumentation that optimizes workflow and can be accomplished by one person.

Figure 1:
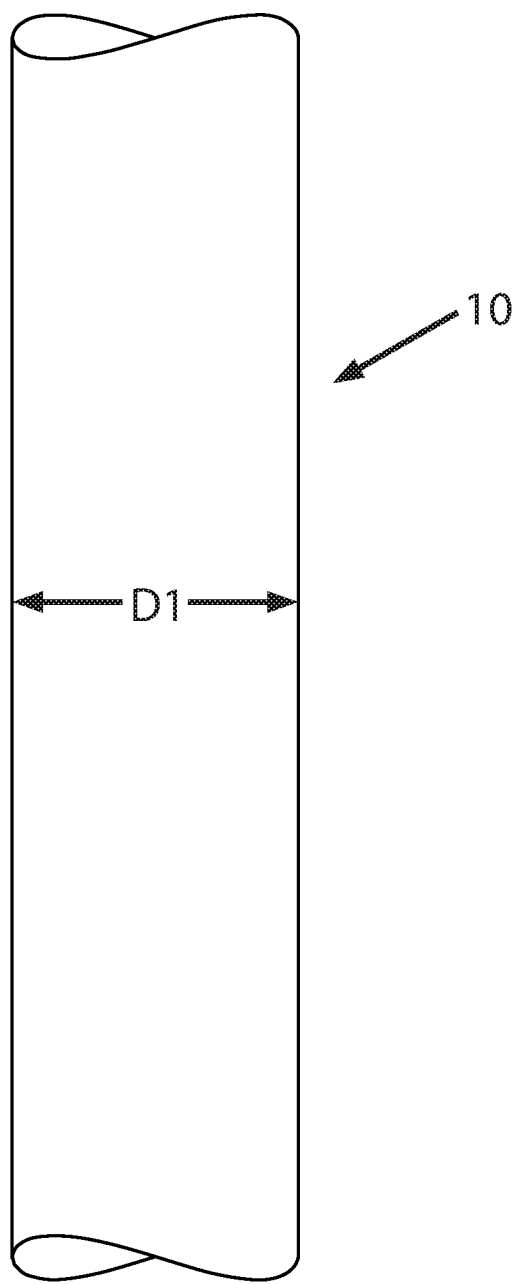
FIG. 1 is a schematic side elevation view of a segment of a prior art tensile member.

The anchor, installation system, and installation method described herein are suitable for receiving and securing a tensile member to bone. The term "tensile member" as used herein generally refers to any flexible element capable of transmitting a tensile force. Nonlimiting examples of known types of tensile members include sutures and orthopedic cables. FIG. 1 illustrates a short segment of a representative tensile member 10 having a diameter "D1". Commercially-available tensile members intended to be implanted in the human body may have a diameter "D1" ranging from tens of microns in diameter to multiple millimeters in diameter. Commercially-available tensile members may be made from a variety of materials such as polymers or metal alloys. Nonlimiting examples of suitable materials include absorbable polymers, nylon, ultrahigh molecular weight polyethylene ("UHMWPE") or polypropylene titanium alloys, or stainless steel alloys. Known physical configurations of tensile members include monofilament, braided, twisted, woven, and wrapped.

Figure 2:
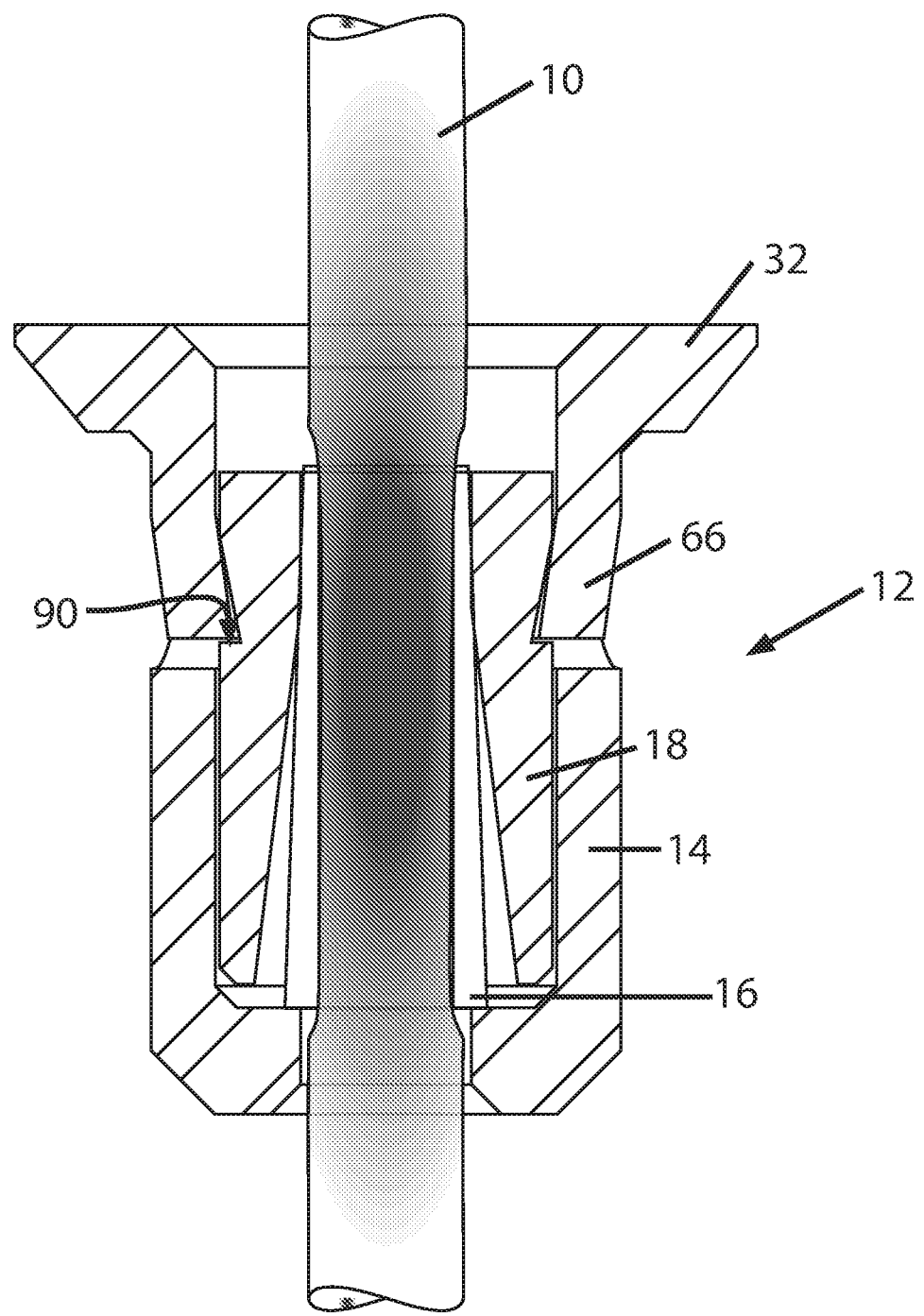
FIG. 2 is cross-sectional view of an assembled anchor with a tensile member engaged therein.
Figure 3:
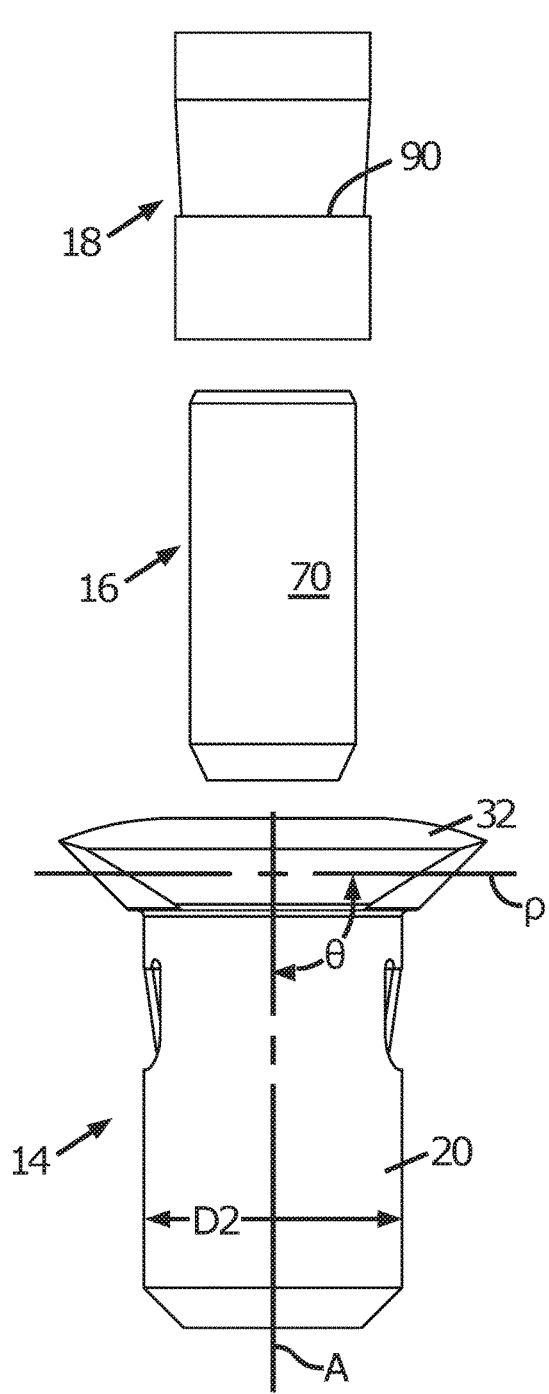
FIG. 3 is an exploded view of the anchor of FIG. 2.

FIG. 2 illustrates an exemplary embodiment of an anchor 12. The anchor 12 includes three functional elements, namely a housing 14 configured to be implanted into bone, a collet 16 received in the housing 14 and configured to be swaged around and against a tensile member 10 without moving axially relative to the housing 14 or tensile member 10, and a sleeve 18 received in the housing 14 which is capable of moving axially within the housing 14 so as to swage the collet 16, thus retaining the tensile member 10. Each of these basic elements is described in detail below with reference to FIGS. 3 and 4.

The housing 14 has a body 20 extending along a central axis "A" between first and second ends 22, 24. The body 20 is defined by a peripheral wall 26 having interior and exterior surfaces 28, 30 respectively, and defining a hollow interior 29. In the illustrated example, the body 20 is generally cylindrical in shape. The first and second ends 22, 24 of the body 20 may be chamfered and/or radiused as illustrated or otherwise shaped to ease insertion into bone. The first end of the body 22 has an internal flange 31 which is sized to define a stop against axial motion of the collet 16.

Figure 4:
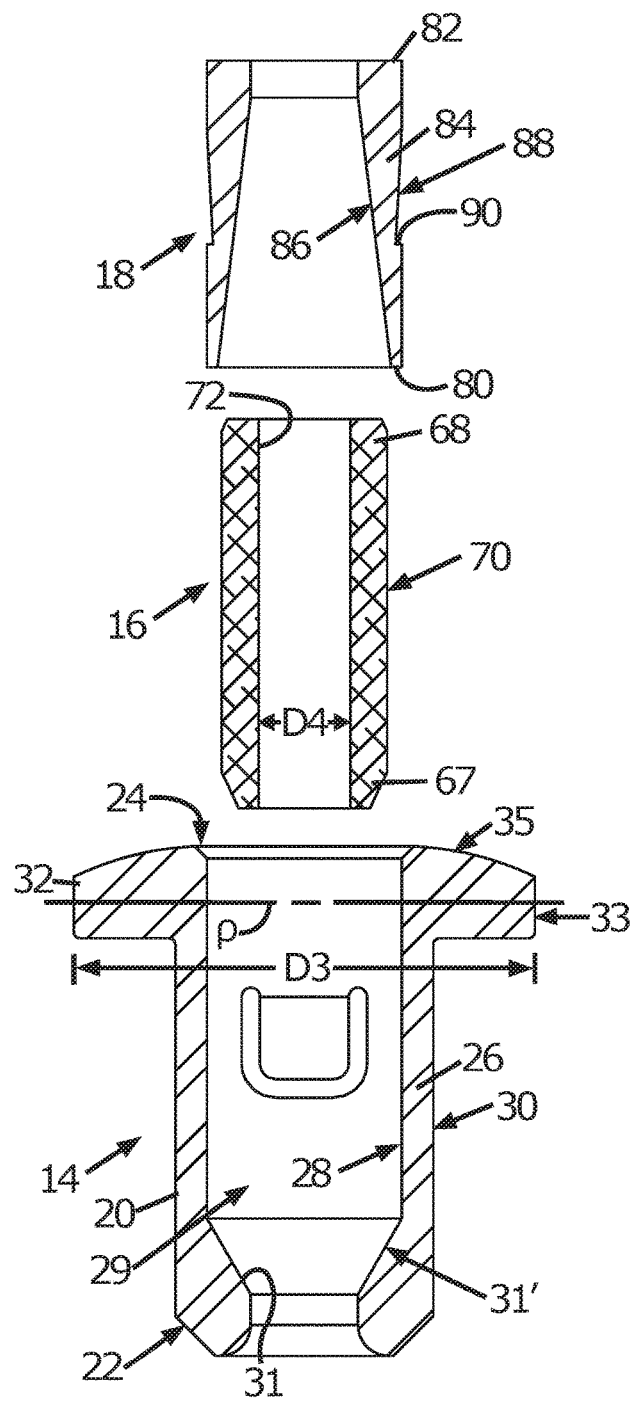
FIG. 4 is a cross-sectional view of FIG. 3.
Figure 5:
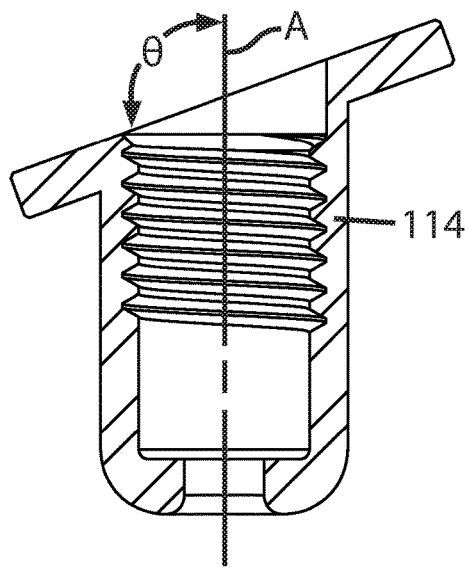
FIG. 5 is a schematic cross-sectional view of a housing having a flange disposed at an oblique angle.

A generally annular flange 32 is located at or near the second end 24 and extends radially outwards from the body 20. The flange 32 defines lateral and axial surfaces 33, 35 respectively. The size and shape of the flange 32 may be selected to suit a particular application. In the example illustrated in FIG. 4, a reference plane "P" passing through the flange 32 is oriented at an angle θ perpendicular to the central axis A. It will be understood that the orientation of the flange may be varied to suit a particular application. For example, FIG. 5 shows a housing 114 in which the angle θ is oblique to the central axis A.

The anchor 12 may have an overall size which is generally small enough to be implanted inside a human body. In one example the housing 14 may be cylindrical in shape with an outside diameter "D2" of about 3 to 12 mm, and the flange 32 may have an outside diameter "D3" about 5 to 20 mm.

The exterior surface 30 of the housing 14, specifically the body 20 may be configured (in terms of structure, material selection, or both) to improve the connection between the housing 14 and the bone. Examples of exterior surfaces configured to achieve this function are illustrated in FIGS. 6, 7, and 8.

Figure 6:
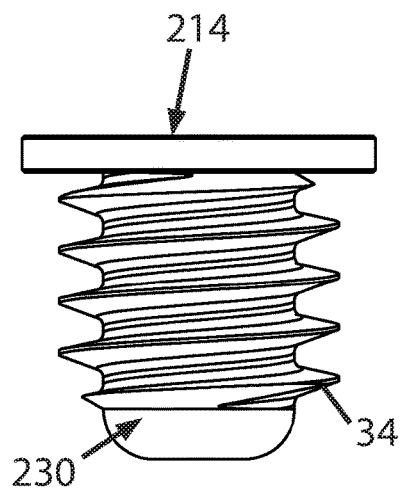
FIG. 6 is a schematic side elevation view of a housing having an exterior surface including male threads.

FIG. 6 shows a housing 214 in which an exterior surface 230 of the body is formed into male threads 34.

Figure 7:
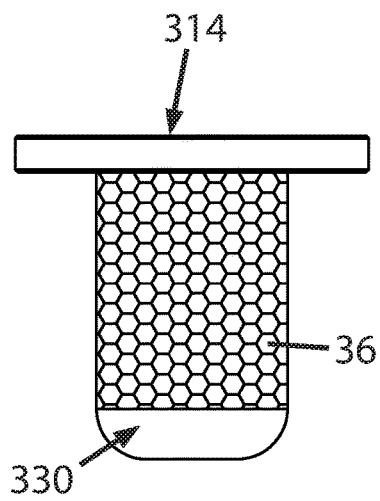
FIG. 7 is a schematic side elevation view of a housing having an exterior surface including a surface coating.

FIG. 7 shows a housing 314 in which an exterior surface 330 of the body has a coating 36 applied thereto which encourages bone growth. One example of a known type of coating that encourages bone growth and infiltration is an inorganic crystalline structure such as hydroxyapatite ("HA").

Figure 8:
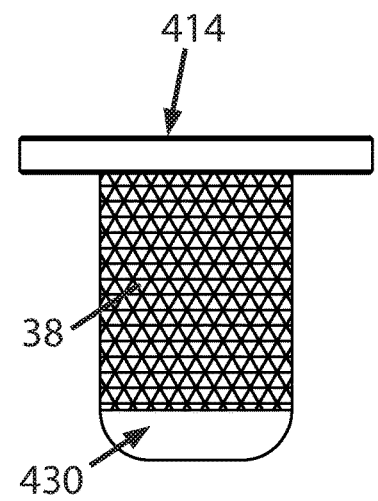
FIG. 8 is a schematic side elevation view of a housing having an exterior surface incorporating knurling.

FIG. 8 shows a housing 414 in which an exterior surface 430 of the body has a surface texture 38 incorporating areas which are relatively raised interspersed with areas that a relatively lowered. One example of a known type of surface texture is knurling.

The housing 14 may incorporate a connection feature configured to permit a secure, releasable connection to an instrument used for insertion or manipulation of the anchor 12. Examples of connection features are illustrated in FIGS. 9-17. At least some of these connection features permit disconnection of the instrument without applying a torsional force to the housing 14.

FIG. 9 shows a housing 514 incorporating female threads 40 which engage male threads 42 of an insertion instrument (shown generically at "I").

FIG. 10 shows a housing 614 having a flange incorporating male threads 44 which engage female threads 48 of an insertion instrument I.

FIGS. 11 and 12 show a housing 714 having internal slots 50 which receive external lugs 52 formed on the periphery of an insertion instrument I, forming a "bayonet" type connection.

FIGS. 13 and 14 show a housing 814 having circumferential slots 54 formed in the flange 32 which receive cylindrical lugs 55 formed on an end surface of an insertion instrument I.

FIG. 15 shows a housing 914 having a counterbore 56 formed therein sized to receive collet jaws 58 formed on an insertion instrument I.

FIGS. 16 and 17 show a housing 964 connected to a distal end of an insertion instrument I by an integral collar 965 which is perforated with openings 966. In use, insertion instrument I may be used to implant the housing 964, and secure the tensile member 10. The collar 965 may then be fractured in order to detach insertion instrument I. This may be described as a "breakaway" connection.

The housing 14 may incorporate a sleeve retention feature configured to retain the sleeve 18 in an activated position. These features interact with retention features of the sleeve 18 which are described in more detail below. Examples of sleeve retention features are illustrated in FIGS. 18-20.

FIG. 18 shows a housing 1014 incorporating a tapered section 60 in the interior surface 1028 of the peripheral wall. The tapered section 60 is located near the first end 1022 of the body 1020.

FIG. 19 shows a housing 1114 in which the interior surface 1128 of the peripheral wall 1126 incorporates a circumferential groove 62 which receives a resilient snap ring 64.

FIG. 20 shows a housing 1214 in which the peripheral wall 1226 defines one or more integral resilient locking tabs 66 that extend radially inward.

The housing 14 may be made from any material which is biocompatible and which will engage the other elements so as to transfer tensile force thereto. As used herein, the term "biocompatible" refers to a material which is not harmful to living tissue. Nonlimiting examples of suitable materials for the housing 14 include polymers and metal alloys. Nonlimiting example of suitable metal alloys include stainless steel alloys and titanium alloys. The housing 14 may be fabricated by a technique such as machining, forging, casting, sintering, or additive manufacturing (e.g., "3D printing"). Optionally, the housing 14 may comprise a porous material.

The housing 14 may be treated with known coating such as titanium nitride, chrome plating, carbon thin films, and/or diamond-like carbon coatings.

The housing 14 may allow for the placement of a cap after implantation to protect the pieces inside or to create a smoother surface. Examples are shown in FIGS. 40-43.

Figures 40, 41:
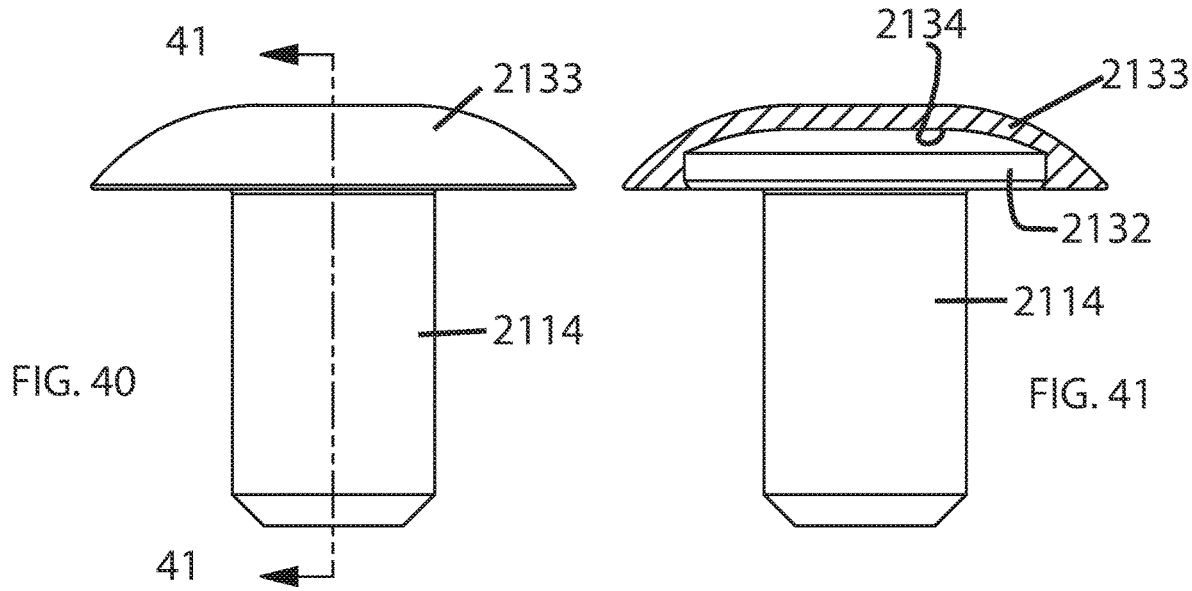
FIG. 40 is a schematic side elevation view of an exemplary housing assembled with a snap-on cap.
FIG. 41 is a sectional view of the housing and cap of FIG. 40.

FIGS. 40 and 41 illustrate a housing 2114 with a flange 2132. A smooth, convex-curved cap 2133 includes an internal recess 2134 closely matched to the exterior shape of the flange 2132 so that the cap 2133 can engage the flange 2132 in a snap-fit relationship.

Figures 42, 43:
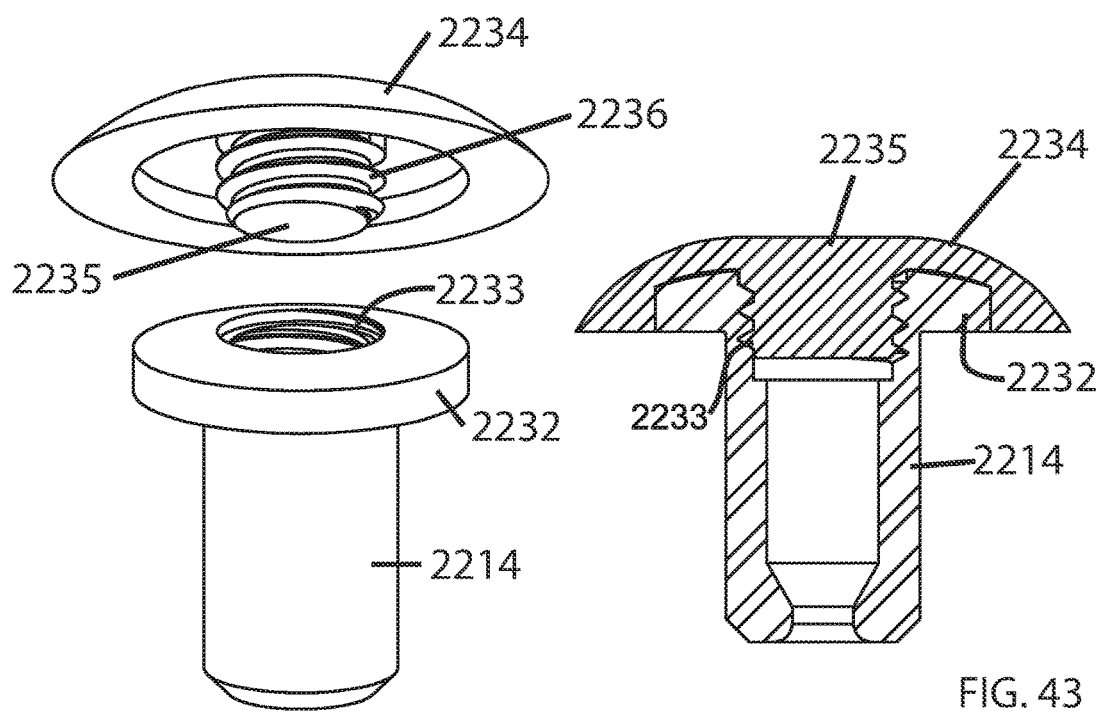
FIG. 42 is a schematic exploded perspective view of an exemplary housing assembled with a screw-on cap.
FIG. 43 is a sectional view of the housing and cap of FIG. 42.

FIGS. 42 and 43 illustrate a housing 2214 with a flange 2232 and internal threads 2233. A cap 2234 with a smooth, convex-curved exterior includes a central stud 2235 with external threads 2236 that can engage internal threads 2233 to secure the cap 2234 to the housing 2214.

Referring back to FIGS. 3 and 4, the collet 16 is a hollow member with first and second ends 67, 68 and an exterior surface 70. The collet 16 has a central bore 72 which is sized to receive the tensile member 10 described above. For example, the central bore 72 may be cylindrical, with a diameter "D4" which is initially slightly larger than a diameter D1 of the tensile member 10. The central bore 72 need not have a circular cross-section; the cross-section may be a polygon shape (e.g. triangular, square) or it may be a lobed shape (e.g., triangular with radiused corners) or spline shaped.

The collet 16 is configured so as to readily permit it to be swaged, i.e. shaped in such a manner to reduce its cross-section and the size of the central bore 72 so that it firmly engages the tensile member 10 and allows a tensile force to be applied thereto. The act of swaging may involve the collet 16 being deformed, crushed, collapsed, or compressed. The collet 16 is configured, e.g., sized and shaped, such that when subjected to pressure from the sleeve 18, it will abut the internal flange 31 of the body 20, thus stopping its further axial movement, and permitting the swaging action (described in more detail below) to take place without axial movement of the collet 16 relative to the tensile member 10 or housing 14.

The exterior surface 70 has a shape adapted to interact with the interior surface of the sleeve 18 described below so as to produce a radially inwardly directed force on the collet 16 in response to the axial movement of the sleeve 18. Fundamentally, at least one of the exterior surface 70 of the collet 16 and the interior surface of the sleeve 18 incorporates a taper i.e., a diameter or lateral dimension which is larger near the first end and smaller near the second end of the respective element. In the example shown in FIGS. 3 and 4, the exterior surface 70 is cylindrical with chamfered ends. FIGS. 21-26 generally show alternative collets where the peripheral exterior surface is tapered, defining a shape like a frustum of a cone.

Additionally, the internal flange 31 of the housing 14 and the exterior surface 70 may be configured such that axial movement of the collet 16 towards the first end 22 causes a radially inwardly directed force on the collet 16. For example, FIG. 4 illustrates a transition section 31' adjacent the interface of the internal flange 31 in the cylindrical portion of the interior surface 28. The shaping of this transition section 31' may be tailored to control the direction and magnitude of a radially-inward force applied to the collet 16. In general, the transition section defines a constriction adjacent the internal flange 31. In the illustrated example, the transition section 31' is a straight taper or generally conical section; other shapes such as chamfers, fillets, curves, splines, etc. may be used.

The collet 16 may be made from any material which will engage the tensile member 10 so as to transfer tensile force thereto and which can be successfully swaged. Nonlimiting examples of suitable materials include polymers and metal alloys. One nonlimiting example of a suitable metal alloy is an aluminum alloy. The collet 16 may be fabricated by a technique such as machining, forging, casting, sintering, or additive manufacturing (e.g., "3D printing"). The collet 16 may be made from a material which has a lower effective elastic modulus than the sleeve 18, or stated another way, is "softer" than the sleeve 18. Optionally, the collet 16 may comprise a porous material.

Optionally, the collet 16 may be coated with a low-friction coating such as diamond-like carbon ("DLC").

Optionally, the collet 16 may incorporate a geometry having sections of removed material or "negative space" which is configured to facilitate collapse of the collet 16, so as to optimize stress around the tensile member 10. Examples of collapsing geometries are illustrated in FIGS. 21-26.

FIGS. 21 and 22 show a collet 116 having a longitudinal through slot 74 formed on one side, and a longitudinal groove 76 formed opposite the through slot 74.

FIGS. 23 and 24 show a collet 216 having a plurality of curvilinear openings 77 formed through the wall thereof, providing a negative space that allows the collet 216 to collapse inwards.

FIGS. 25 and 26 show a collet 316 having a plurality of longitudinal through slots 78 formed in the wall thereof, each slot 78 being open to at least one end and extending less than the full length of the collet 316. The through slots 78 are arranged to define a spring-like structure.

Referring back to FIGS. 3 and 4, the sleeve 18 is a hollow member with open first and second ends 80, 82 The sleeve 18 is sized is such that the tensile member 10 described above can pass through the first and second ends 80, 82. The sleeve 18 is defined by a peripheral wall 84 having interior and exterior surfaces 86, 88, respectively. In the illustrated example, the sleeve 18 is generally cylindrical in shape.

The interior surface 86 has a shape adapted to interact with the exterior surface 70 of the collet 16 described above so as to produce a radially inwardly directed force on the collet 16 in response to the axial movement of the sleeve 18. As noted above, at least one of the exterior surface 70 of the collet 16 and the interior surface 86 of the sleeve 18 incorporates a taper i.e., a diameter or lateral dimension which is larger near the first end and smaller near the second end of the respective element. In the example shown in FIGS. 3 and 4, the interior surface 86 is tapered, defining a shape like a frustum of a cone, with a larger diameter at the first end 80.

The interior surface 86 of the sleeve 18 may have various geometries selected to optimize the swaging force. The interior surface 86 of the sleeve 18 shown in FIG. 4 has a one-way taper. Examples of alternative compression surface geometries are illustrated in FIGS. 27-29.

Figure 27:
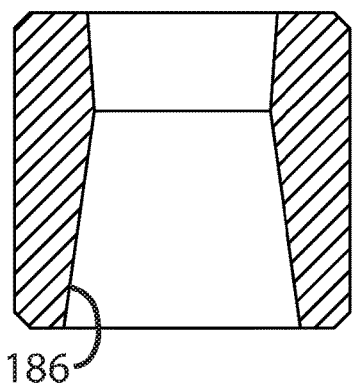
FIG. 27 is a schematic cross-sectional view of a sleeve having a double taper interior surface.

FIG. 27 shows an interior surface 186 with a two-way taper.

Figure 28:
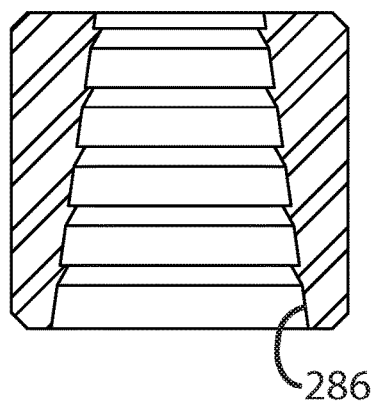
FIG. 28 is a schematic cross-sectional view of a sleeve having a scaled interior surface.

FIG. 28 shows an interior surface 286 having a series of step-like faces defining a "scaled" geometry.

Figure 29:
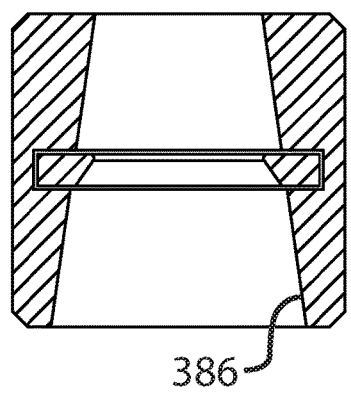
FIG. 29 is a schematic cross-sectional view of a sleeve having an integral snap ring interior surface.

FIG. 29 shows an internal surface 386 with an integral snap ring geometry.

The sleeve 18 may incorporate a retention feature which cooperates with the sleeve retention feature of the housing described above in order to retain the sleeve 18 in an activated position. FIG. 4 illustrates an exemplary retention feature in the form of an annular step 90 formed in the exterior surface 88 of the sleeve 18.

The sleeve 18 may be made from any material which is biocompatible and which can receive axial force and transfer radial compressive force to the collet 16. Nonlimiting examples of suitable materials include polymers and metal alloys. One nonlimiting example of a suitable metal alloy is a stainless steel alloy. The sleeve 18 may be fabricated by a technique such as machining, forging, casting, sintering, or additive manufacturing (e.g., "3D printing"). Optionally, the sleeve 18 may comprise a porous material.

All or a portion of the sleeve 18 may be provided with a known coating such as titanium nitride, chrome plating, carbon thin films, and/or diamond-like carbon coatings.

Figure 30:
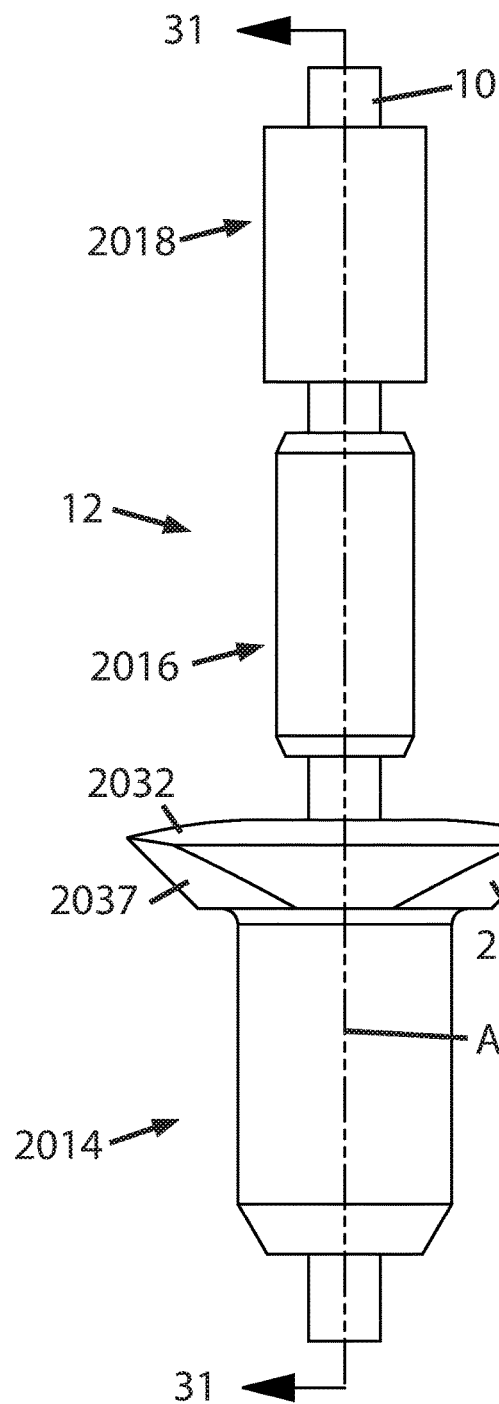
FIG. 30 is an exploded view of another exemplary embodiment of an anchor.
Figure 31:
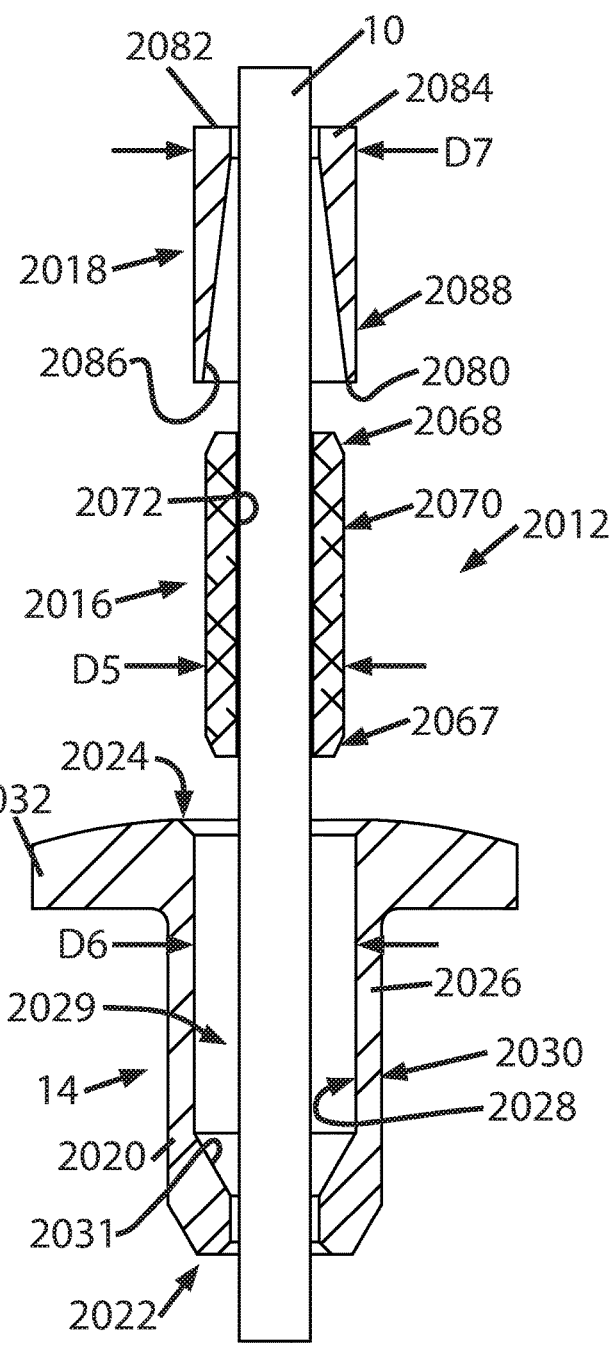
FIG. 31 is a cross-sectional view of FIG. 30.

FIGS. 30-37 illustrate another exemplary embodiment of an anchor, denoted 2012 generally. The anchor 2012 is generally similar in construction to the anchor 12 described above. Any elements of the anchor 2012 not specifically described may be taken to be identical to those of the anchor 12. Referring to FIGS. 30 and 31, the anchor 2012 includes a housing 2014, a collet 2016 received in the housing 2014, and a sleeve 2018 received in the housing 2014 which is capable of moving axially within the housing 2014 so as to swage the collet 2016, thus retaining the tensile member 10.

The housing 2014 has a body 2020 extending along a central axis "A" between first and second ends 2022, 2024. The body 2020 is defined by a peripheral wall 2026 having interior and exterior surfaces 2028, 2030 respectively, and defining a hollow interior 2029. In the illustrated example, the body 2020 is generally cylindrical in shape. The first end of the body 2022 has an internal flange 2031 which is sized to define a stop against axial motion of the collet 2016.

A generally annular flange 2032 is located at or near the second end 2024 and extends radially outwards from the body 2020. In the example illustrated in FIGS. 30 and 31, the flange 2032 incorporates chamfered surfaces 2037 which are configured to engage jaws of an insertion instrument is described in more detail below.

The exterior surface 2030 of the housing 2014 may be configured to improve the connection between the housing 2014 and the bone. Examples of exterior surfaces configured to achieve this function are described above and illustrated in FIGS. 6, 7, and 8.

The housing 2014 may incorporate a connection feature configured to permit a secure, releasable connection to an instrument used for insertion or manipulation of the anchor 2012. Examples of connection features are described above and illustrated in FIGS. 9-17.

The housing 2014 may incorporate a sleeve retention feature configured to retain the sleeve 2018 in an activated position. These features interact with retention features of the sleeve 2018 which are described in more detail below. In the illustrated example, the retention feature is a dimension (e.g., diameter) "D6" of the interior surface 2028 which is selected to provide a predetermined fit with the sleeve 2018, as described in more detail below.

The collet 2016 is a hollow member with first and second ends 2067, 2068 and an exterior surface 2070. The collet 2016 has a central bore 2072 which is sized to receive the tensile member 10 described above. For example, the central bore 72 may be cylindrical, with a diameter "D5" which is initially slightly larger than a diameter D1 of the tensile member 10. The central bore 2072 need not have a circular cross-section; the cross-section may be a polygon shape (e.g. triangular, square) or it may be a lobed shape (e.g., triangular with radiused corners).

The collet 2016 is configured so as to readily permit it to be swaged, i.e. shaped in such a manner to reduce its cross-section and the size of the central bore 2072 so that it firmly engages the tensile member 10 and allows a tensile force to be applied thereto. The act of swaging may involve the collet 2016 being deformed, crushed, collapsed, or compressed. The collet 2016 is configured, e.g., sized and shaped, such that when subjected to pressure from the sleeve 2018, it will abut the internal flange 2031 of the body 2020, thus stopping its further axial movement, and permitting the swaging action to take place without axial movement of the collet 2016 relative to the tensile member 10 or housing 2014.

The exterior surface 2070 has a shape adapted to interact with the interior surface of the sleeve 2018 described below so as to produce a radially inwardly directed force on the collet 2016 in response to the axial movement of the sleeve 2018. Fundamentally, at least one of the exterior surface 2070 of the collet 2016 and the interior surface of the sleeve 2018 incorporates a taper i.e., a diameter or lateral dimension which is larger near one end and smaller near the opposite end of the respective element. In the example shown in FIGS. 30 and 31, the exterior surface 2070 is cylindrical with chamfered ends. The exterior dimensions and shape of the exterior surface 2070 are selected so as to provide a predetermined fit with the sleeve 2018 both before and after a compression process, as described in more detail below.

Additionally, the internal flange 2031 of the housing 2014 and the exterior surface 2070 may be configured such that axial movement of the collet 2016 towards the first end 2022 causes a radially inwardly directed force on the collet 16. Examples of this configuration are described above.

The sleeve 2018 is a hollow member with open first and second ends 2080, 2082. The sleeve 2018 is sized is such that the tensile member 10 described above can pass through the first and second ends 2080, 2082. The sleeve 2018 is defined by a peripheral wall 2084 having interior and exterior surfaces 2086, 2088, respectively. In the illustrated example, the exterior surface 2088 of the sleeve 2018 is generally cylindrical in shape.

The interior surface 2086 has a shape adapted to interact with the exterior surface 2070 of the collet 2016 described above so as to produce a radially inwardly directed force on the collet 2016 in response to the axial movement of the sleeve 2018. As noted above, at least one of the exterior surface 2070 of the collet 2016 and the interior surface 2086 of the sleeve 2018 incorporates a taper i.e., a diameter or lateral dimension which is larger near one end and smaller near the opposite end of the respective element. In the example shown in FIGS. 30 and 31, the interior surface 2086 is tapered, defining a shape like a frustum of a cone, with a larger diameter at the first end 2080.

The interior surface 2086 of the sleeve 2018 may have any of the various geometries described above which are selected to optimize the swaging force.

The sleeve 18 may incorporate a retention feature which cooperates with the sleeve retention feature of the housing described above in order to retain the sleeve 18 in an activated position. In the illustrated example, the retention feature is a dimension (e.g., diameter) "D7" of the exterior surface 2088 which is selected to provide a predetermined fit with the sleeve 2018 both before and after a compression process, as described in more detail below.

FIGS. 34-37 illustrate the engineered interference lock feature of the anchor 2012. Referring to FIGS. 34 and 35, in the assembled, but uncompressed condition, there is a small clearance between the inside diameter D6 of the housing 2014 and the outside diameter D7 of the sleeve 2018. There is also a small clearance between the inside diameter D5 of the collet 2016 and the outside diameter D1 of the tensile member 10.

FIGS. 36 and 37 illustrate the anchor 2012 in the compressed or actuated condition (e.g. after being compressed by one of the insertion instruments described herein). There is a predetermined interference fit between the inside diameter D6 of the housing 2014 and the outside diameter D7 of the sleeve 2018. This occurs because the sleeve 2018 is forced radially outwards as it is pushed axially over the collet 2016. Furthermore, there is a predetermined interference fit between the inside diameter D5 of the collet 2016 and the outside diameter D1 of the tensile member 10. In this compressed condition, the tensile member 10 is significantly compressed radially and held by the housing-sleeve-collet concentrically compressed configuration.

The materials and/or coatings used in the construction of the housing 2014, collet 2016, and sleeve 2018 may be as described for the housing 14, collet 16, and sleeve 18 described above.

All or a portion of the anchors described above may be made as part of an integral, unitary, or monolithic whole. This may be accomplished, example, by using additive manufacturing process.

Figure 38:
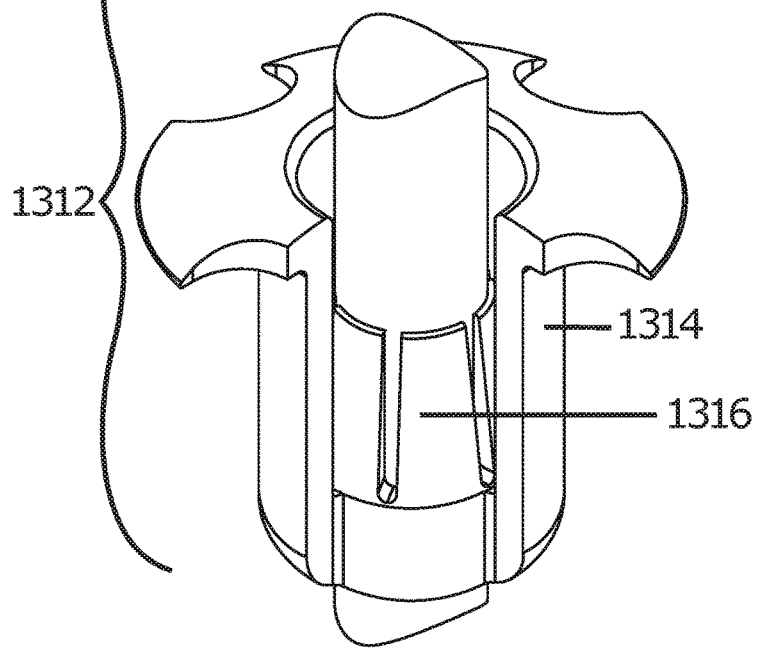
FIG. 38 is a schematic, partially-sectioned perspective view of an exemplary anchor having an integral collet.

FIG. 38 illustrates an exemplary anchor 1312 comprising a housing 1314, a collet 1316, and a sleeve 1318 corresponding to those components as described above. In this example, the collet 1316 is integral, unitary, or monolithic with the anchor 1312. The sleeve 1318 is a separate component.

Figure 39:
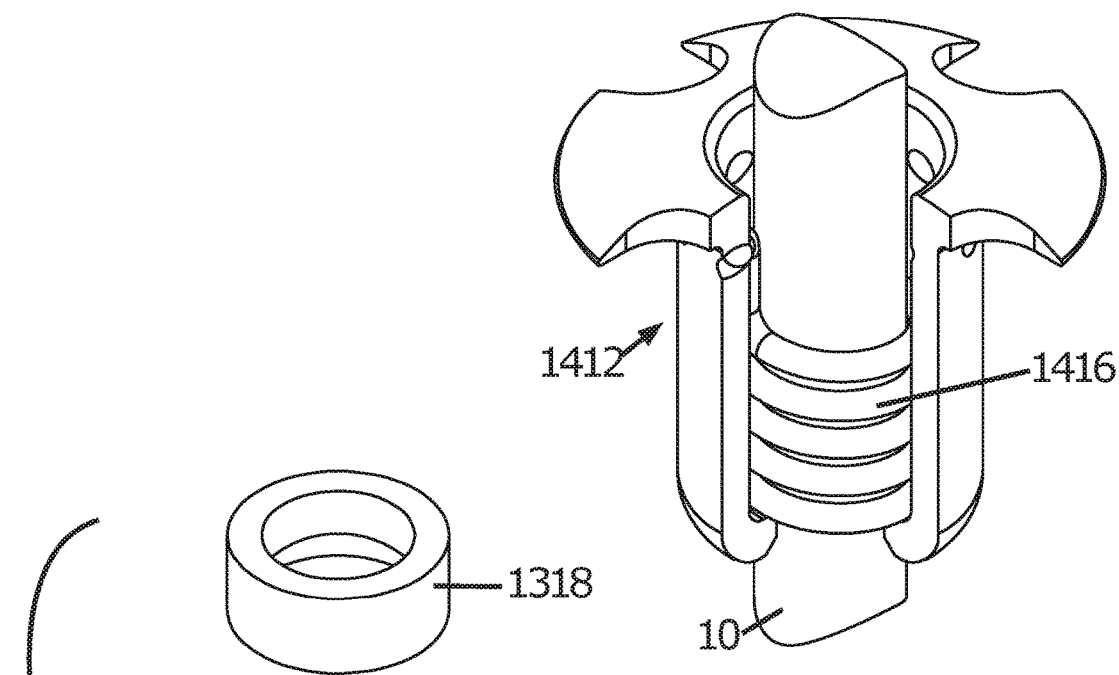
FIG. 39 is a schematic, partially-sectioned perspective view of an exemplary anchor having an integral collet and sleeve.

FIG. 39 illustrates an exemplary anchor 1412 comprising a housing 1414 which receives an internal member 1416. The internal member 1416 is integral, unitary, or monolithic with the anchor 1412. This internal member 1416 is shaped like a tapered coil spring. The bottom end of the coil spring 1416 is held stationary while the top of the coil spring 1416 is allowed to rotate by means of a rotary actuator tool (not shown) that holds the housing 1412 stationary. This tool could be similar to a spanner-type device with pins or lugs and holds the housing 1412 stationary by interfacing with the four locking recesses cut into the flange as shown. When the top of the internal member 1416 is rotated (in this case clockwise), the inner diameter is gradually reduced and constricts around the tensile member 10 to hold it in place axially.

Figure 68:
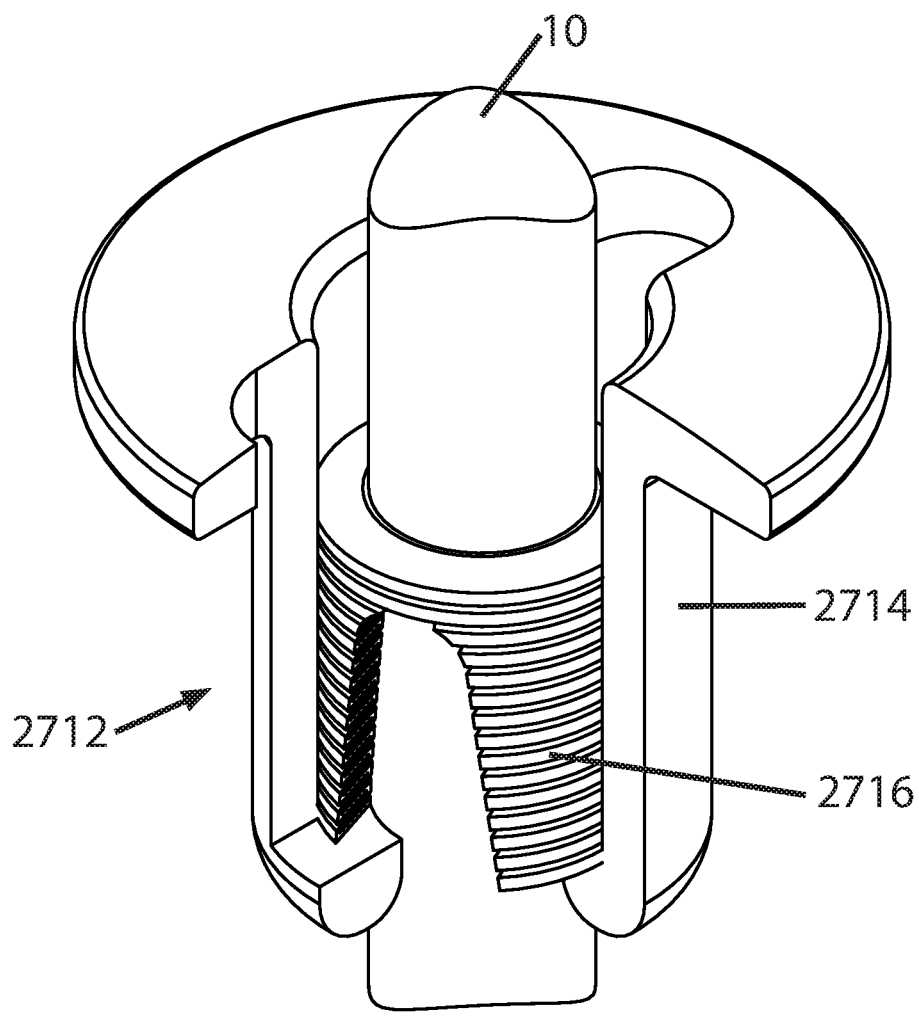
FIG. 68 is a schematic, partially-sectioned perspective view of an exemplary anchor having an integral internal member.

FIG. 68 illustrates an exemplary anchor 2712 comprising a housing 2714 which receives an internal member 2716. This internal member 2716 is shaped like an accordion or wave spring. When compressed axially, the folds deform, bind together, and swage down on the tensile member 10 radially inward. Internal member 2716 thus functions as both a collet and a sleeve. The internal member 2716 optionally may be integral, unitary, or monolithic with the anchor 2712.

Figure 44:
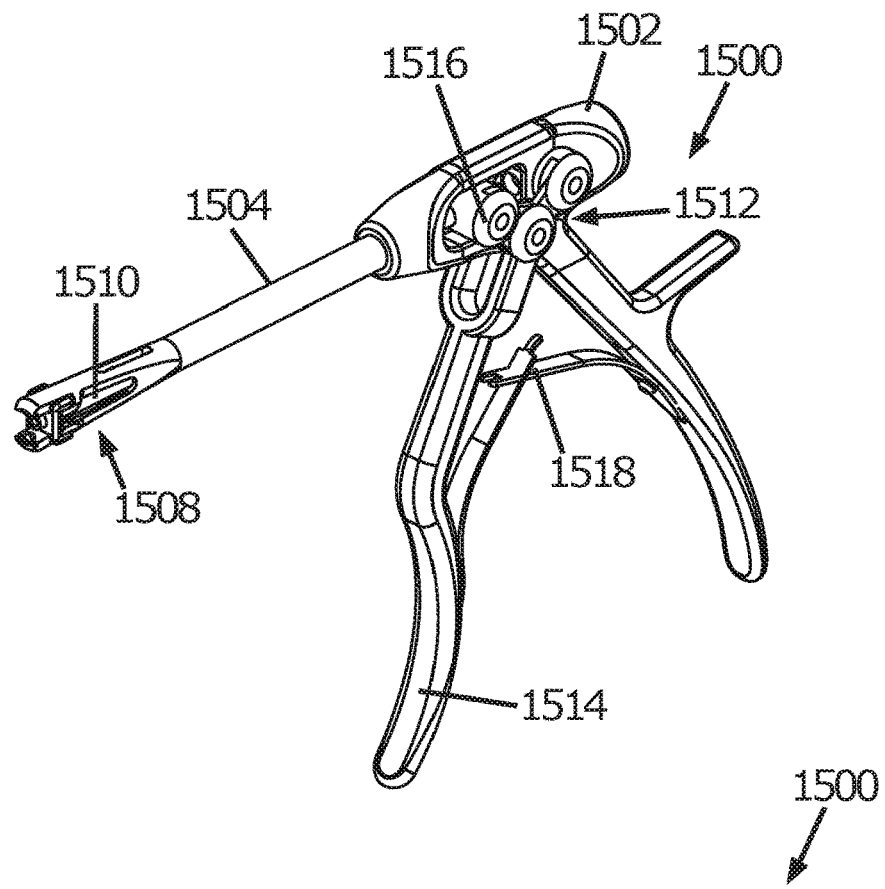
FIG. 44 is a schematic perspective view of an installation instrument for use with the anchor described herein.
Figure 45:
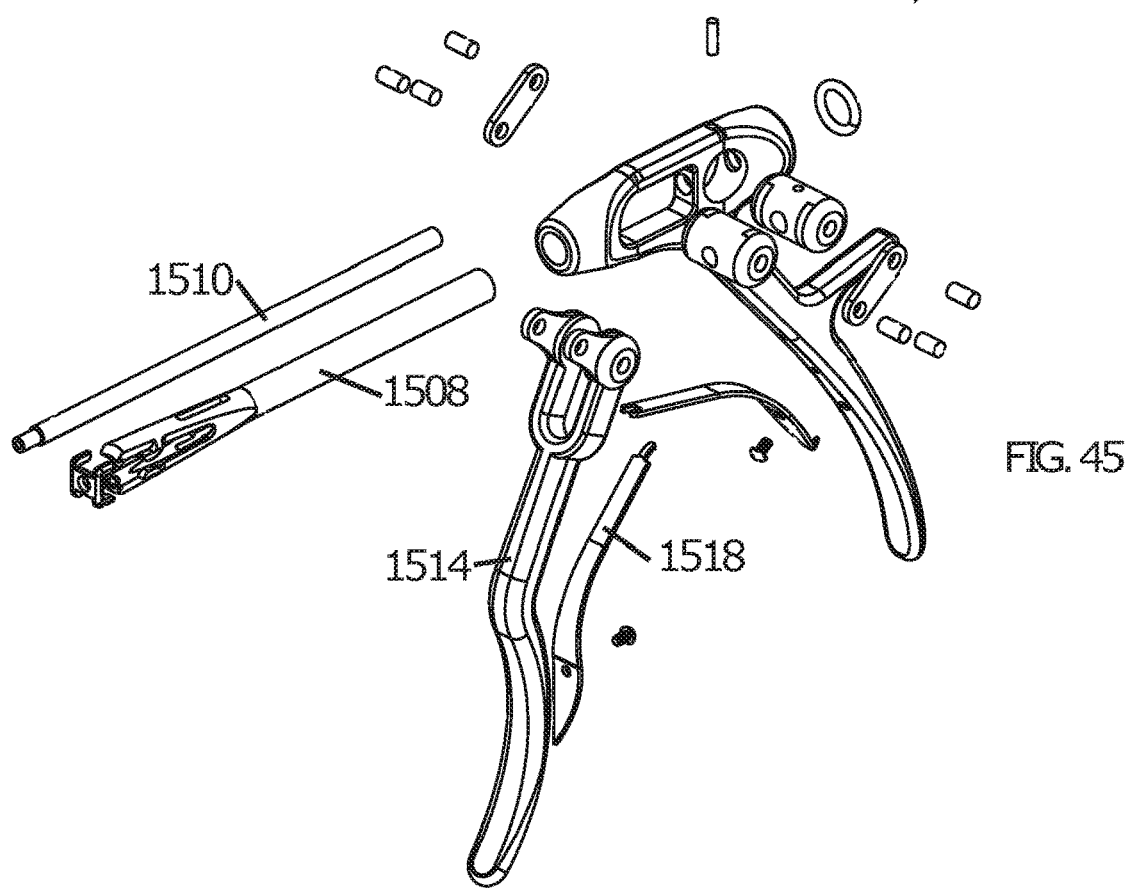
FIG. 45 is an exploded view of the installation instrument of FIG. 44.

FIGS. 44 and 45 an exemplary insertion instrument 1500 which may be used to insert, tension, and activate the anchors 12 described above. The basic components of the insertion instrument 1500 are a body 1502 having a handle, a stem 1504 extending from the body 1502 and having an anchor connection mechanism 1508 disposed at a distal end thereof, a hollow pushrod 1510 extending through the stem 1504 and slidably movable between retracted and extended positions, and a driving mechanism 1512 for moving the pushrod 1510 between retracted and extended positions. The stem 1504 and the pushrod 1510 may be rigid or flexible.

In the illustrated example, the driving mechanism 1512 comprises a toggle linkage 1516 which is manually operated by an operating handle 1514. More specifically, the toggle linkage 1516 is arranged such that when the operating handle 1514 is released, return springs 1518 drive the operating handle 1514, toggle linkage 1518, and pushrod 1510 towards the retracted position, and when the operating handle 1514 is squeezed, it moves the toggle linkage 1516 which in turn extends the pushrod 1510 towards the extended position. The toggle linkage 1516 may be arranged to have a fixed or adjustable range of motion.

It will be understood that the driving mechanism 1512 could be replaced with a different type of mechanical linkage or with the powered devices such as an electrical, pneumatic, or hydraulic actuator (not shown).

Figure 46:
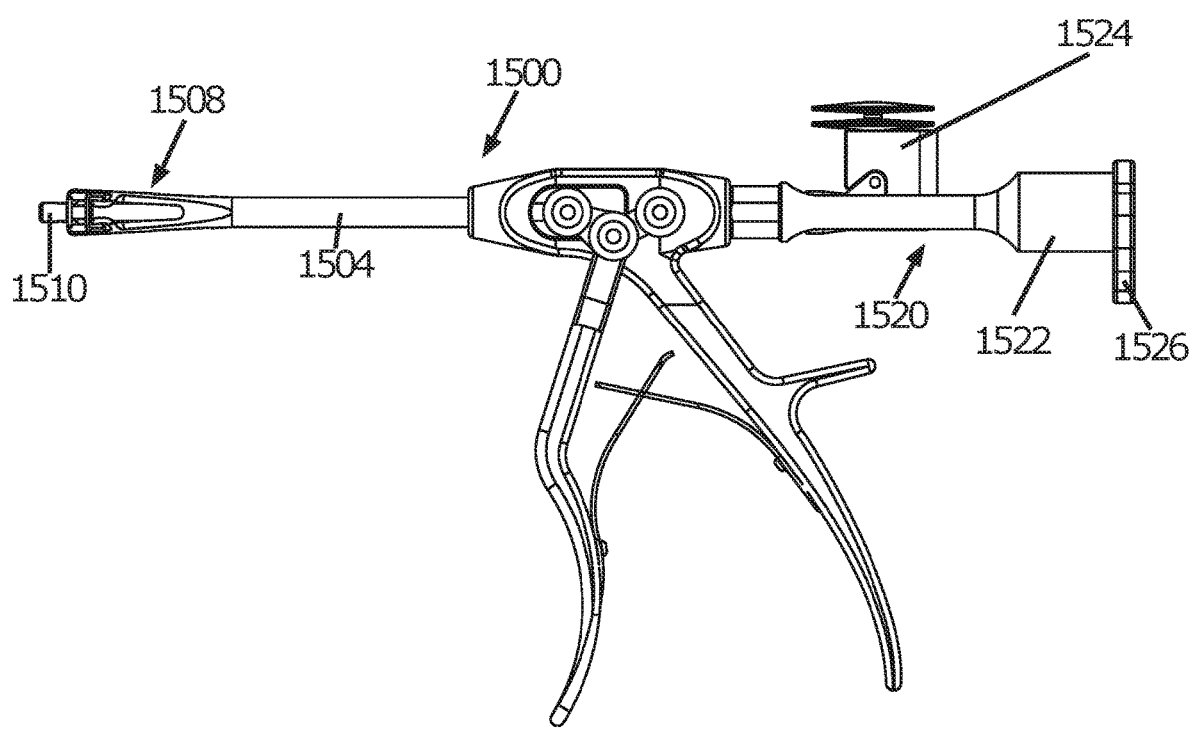
FIG. 46 is a schematic side elevation view of the installation instrument of FIG. 44, with a tensioner attached thereto.

FIG. 46 illustrates an exemplary tensioner 1520 having a housing 1522 which may be connected to the insertion instrument 1500. The tensioner 1522 includes a yoke 1524 configured to clamp a tensile member 10 passing through the pushrod 1510. The yoke 1524 is movable relative to the housing 1522, for example using an internal mechanical driving mechanism (not shown) actuated by an operating knob 1526. Means may be provided for measuring the tension applied to the tensile member 10. For example, the yoke 1524 may be connected to the housing 1522 through a calibrated spring such that the deflection of the yoke 1524 is proportional to applied tension. Alternatively, a calibrated force gauge or other similar mechanism (not shown) may be provided.

Figures 47, 48:
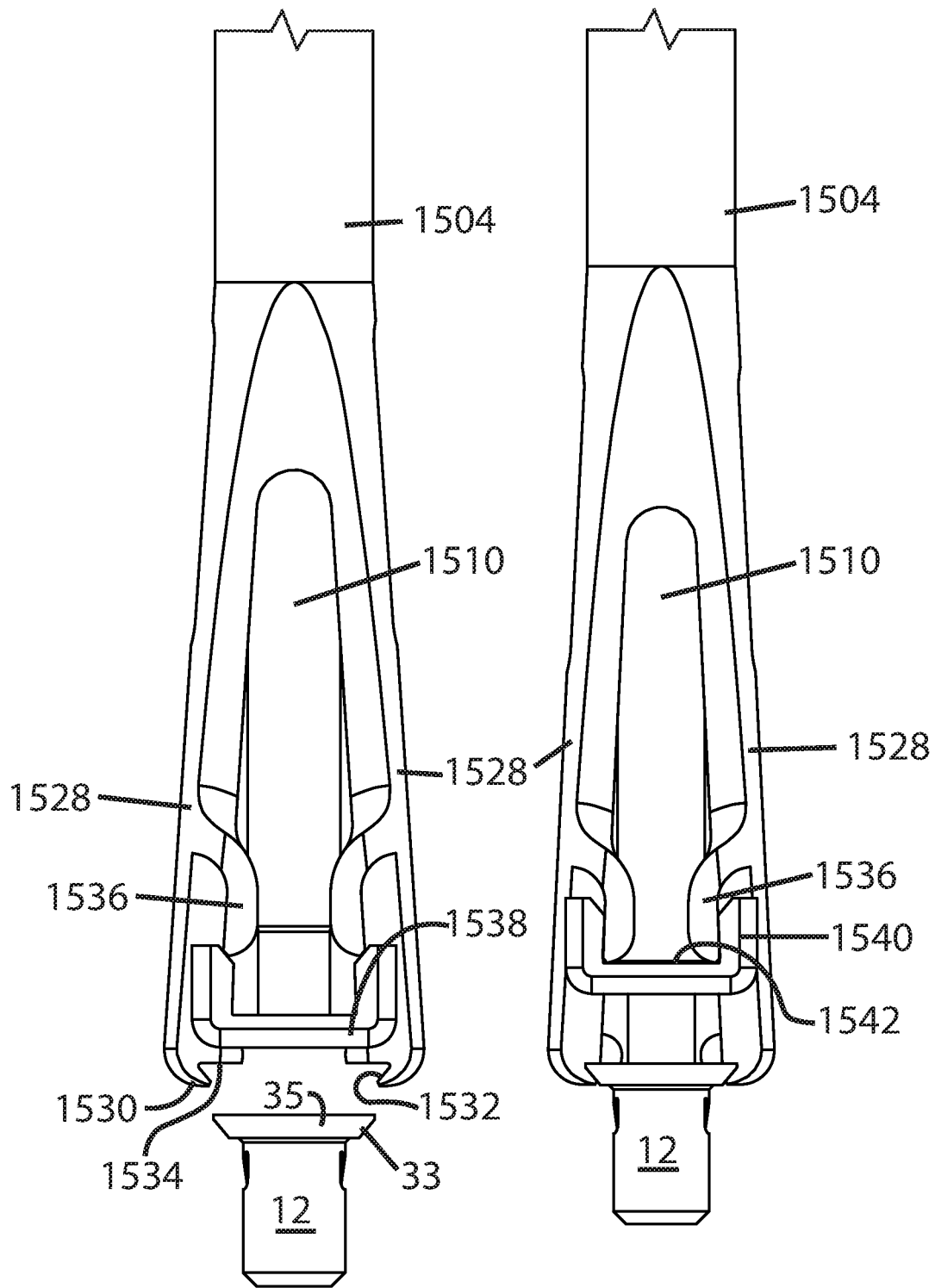
FIG. 47 is a schematic cross-sectional view of a distal end of the stem of the installation instrument of FIG. 44, with jaws thereof in an open position.
FIG. 48 is a view of the stem shown in FIG. 44, with jaws thereof in a closed position.

An exemplary configuration of the stem 1504 and pushrod 1510 are shown in more detail in FIGS. 47 and 48.

The distal end of the stem 1504 incorporates means for engaging and holding an anchor 12. In the illustrated example, the stem 1504 includes a pair of opposed jaws 1528 with tips 1530, which may be formed as integral, spring-like extensions of the stem 1504. The tips 1530 may be formed with lateral and axial engagement surfaces 1532, 1534 respectively, in order to engage lateral and axial faces, 33, 35 respectively of the anchor 12 (shown schematically in FIG. 47). The jaws 1528 are provided with axially-extending hooks 1536 which are set back from the tips 1530. A clip 1538 having a U-shape with axially-extending legs 1540 is disposed laterally between the jaws, in an axial position which is between the tips 1530 and the hooks 1536. The clip 1538 may have an opening 1542 passing therethrough, and the pushrod 1510 may be stepped, having a first portion at its distal end small enough to pass through the opening 1542, and a second portion sufficiently larger to engage the clip 1538.

Figures 32, 33:
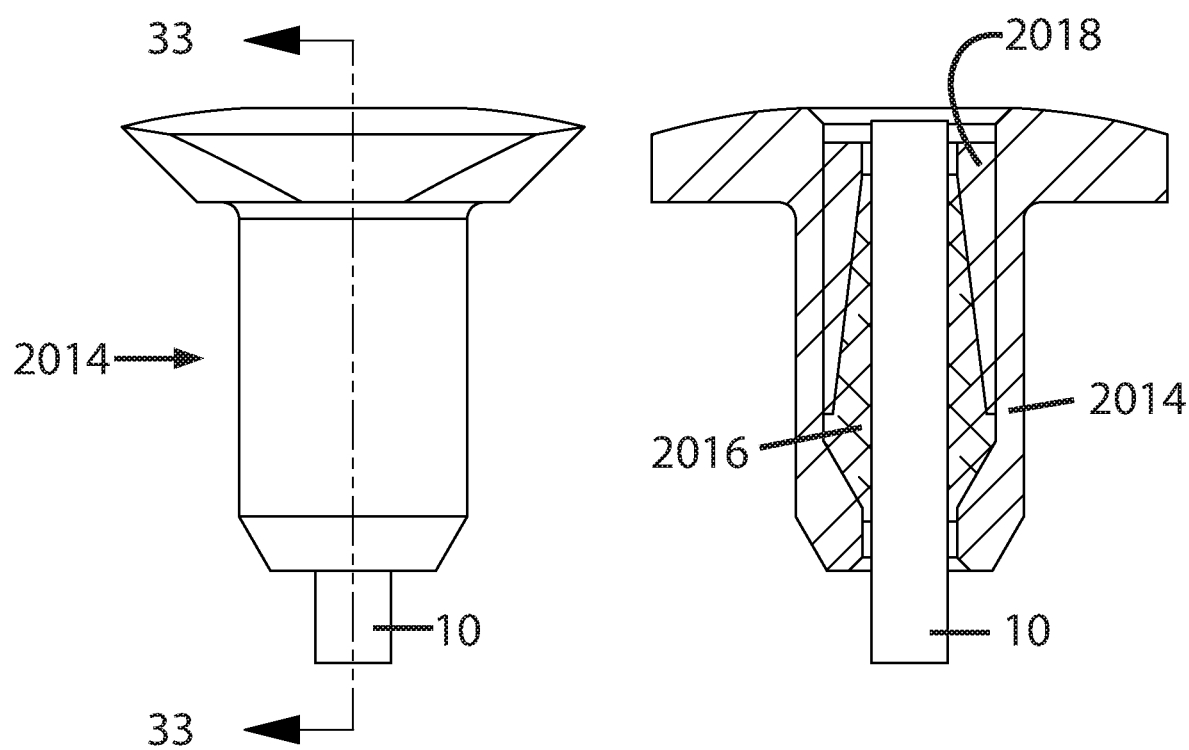
FIG. 32 is a schematic side elevation view of a portion of the anchor of FIG. 30 in a compressed condition.
FIG. 33 is a cross-sectional view of FIG. 32.

FIG. 47 shows the stem 1504 with the pushrod 1510 in a fully extended position, pushing the clip 1538 outwards and spreading the jaws 1528 apart so as to release the anchor 12. FIG. 48 shows the stem 1504 with the pushrod 1510 in a retracted position, allowing the clip 1538 to move inwards, engaging the hooks 1536, thereby pulling the jaws inwards so the tips 1530 engage the flange 32 of the anchor 12. In this position, the anchor 12 is securely held by the stem 1504 and may be manipulated as necessary. The clip 1538 secures the jaws 1528 in the closed position until such time as the pushrod 1510 is actuated, thus disengaging the clip in the jaws as shown in FIG. 33.

Figure 49:
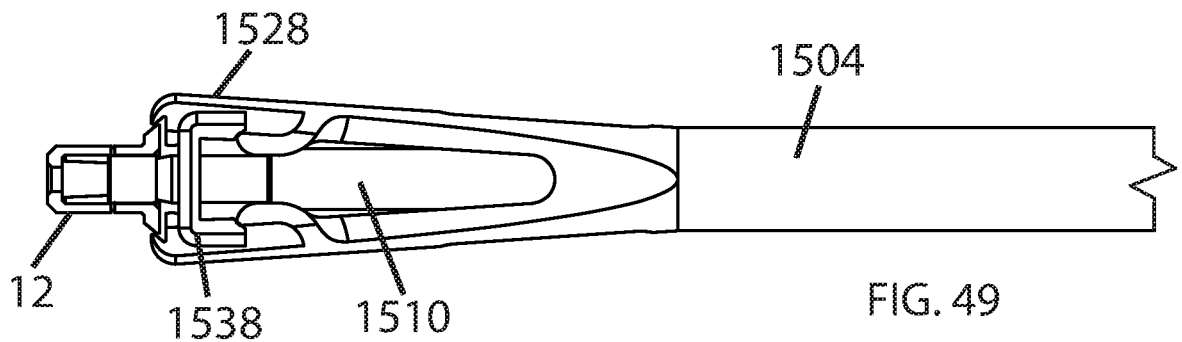
FIG. 49 is a schematic cross-sectional view of a distal end of the stem of the installation instrument of FIG. 44, showing an anchor loaded therein.
Figure 50:
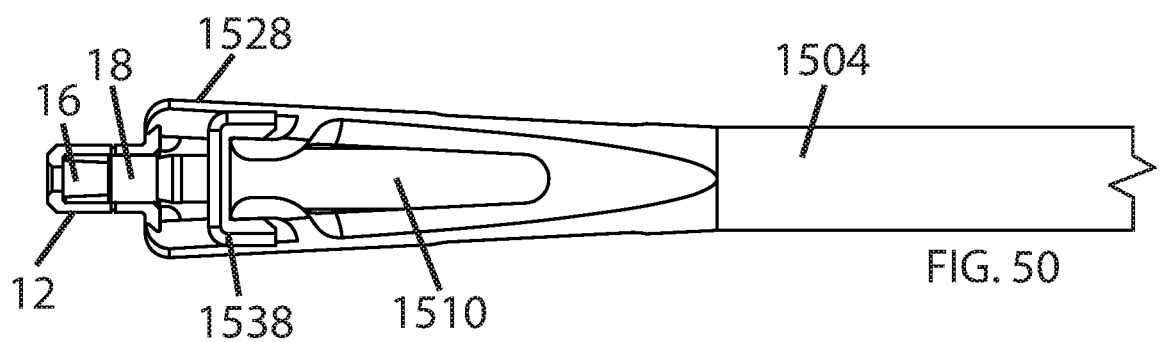
FIG. 50 is a view of the stem of FIG. 49, showing a clip in an engaged position.
Figure 51:
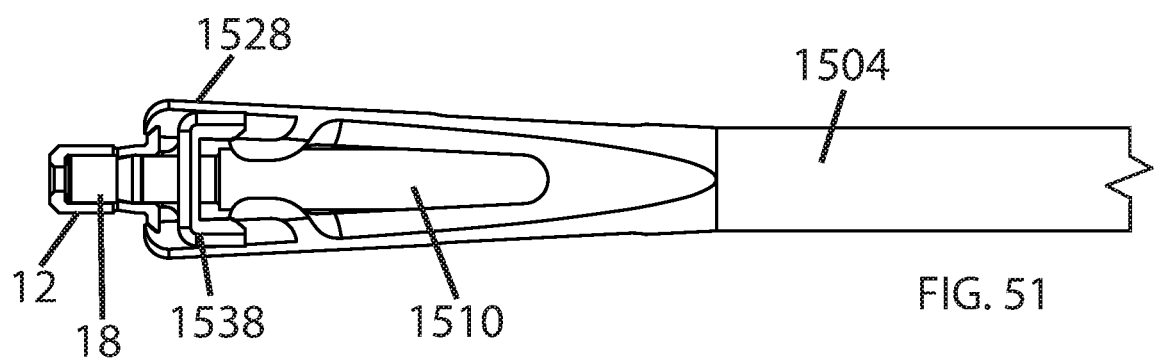
FIG. 51 is another view of the stem of FIG. 49, showing a pushrod thereof being actuated.
Figure 52:
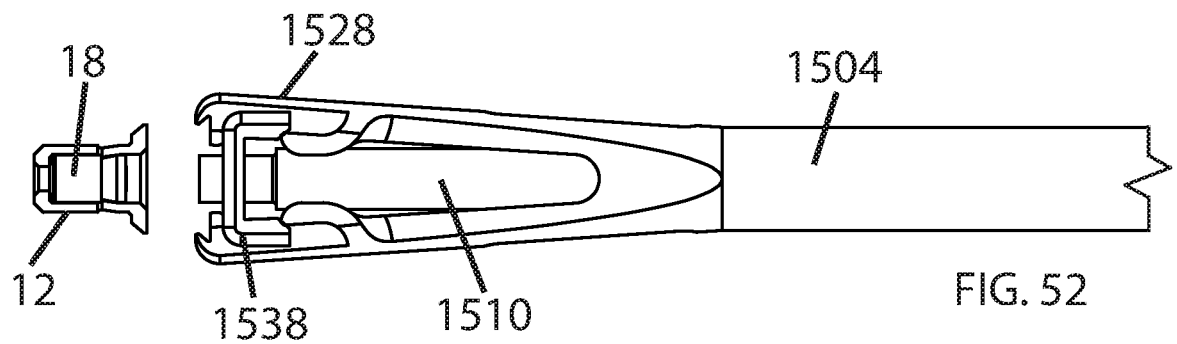
FIG. 52 is another view of the stem of FIG. 49, showing a clip in a released position, with the jaws opened to release the anchor.

FIGS. 49-52 show the sequence of operation of the insertion instrument 1500. FIG. 49 shows an anchor 12 received in the jaws 1528, with the clip 1538 is in a released position. FIG. 50 shows the clip 1538 in an engaged position, holding the jaws 1528 closed. The clip 1538 may be engaged manually, or may be pressed against a tool or fixture (not shown) in order to engage it. FIG. 51 shows the pushrod 1510 being actuated to press the sleeve 18 down over the collet 16. FIG. 52 shows the clip 1538 moved to the released position by the pushrod 1510, and the jaws 1528 open so that the insertion instrument can be removed.

FIGS. 53-58 illustrate an alternative stem 2504 and a method of its operation. The distal end of the stem 2504 includes pair of opposed jaws 2528 with tips 2530, which may be formed as integral, spring-like extensions of the stem 2504. The jaws 2528 flank a pushrod 2510 substantially similar to pushrod 1510 described above. The tips 1530 may be formed with V-shaped engagement surfaces 2532 in order to engage an anchor 12. The V-shaped engagement surfaces 2532 are especially suitable for engaging the chamfered surfaces 2037 of the flange 2032 of the anchor 2012. A generally tubular lock sleeve 2538 having conical end face 2540 surrounds the stem 2504.

FIGS. 53-58 show the sequence of operation of the alternative stem 2504. FIG. 53 shows the lock sleeve 2538 retracted from the jaws 2528. An anchor 2012 is ready to be picked up by the jaws 2538. The anchor 2012 may be held in this position by suitable packaging (not shown).

FIG. 54 shows the jaws 2538 sprung over top of and lightly engaging the flange 2032 of the anchor 2012 with spring pressure.

FIG. 55 shows the lock sleeve 2538 axially slid over the jaws 2538, applying radially inward compressive pressure to the jaws and securely retaining the anchor 2012.

FIGS. 56-57 shows successive stages of actuation of the pushrod to crimp a tensile member 10 in the anchor 2012, substantially as described above.

Three. 58 shows the lock sleeve 2538 retracted from the jaws 2538, allowing the stem 2504 two be detached from the anchor 2012.

Figure 59:
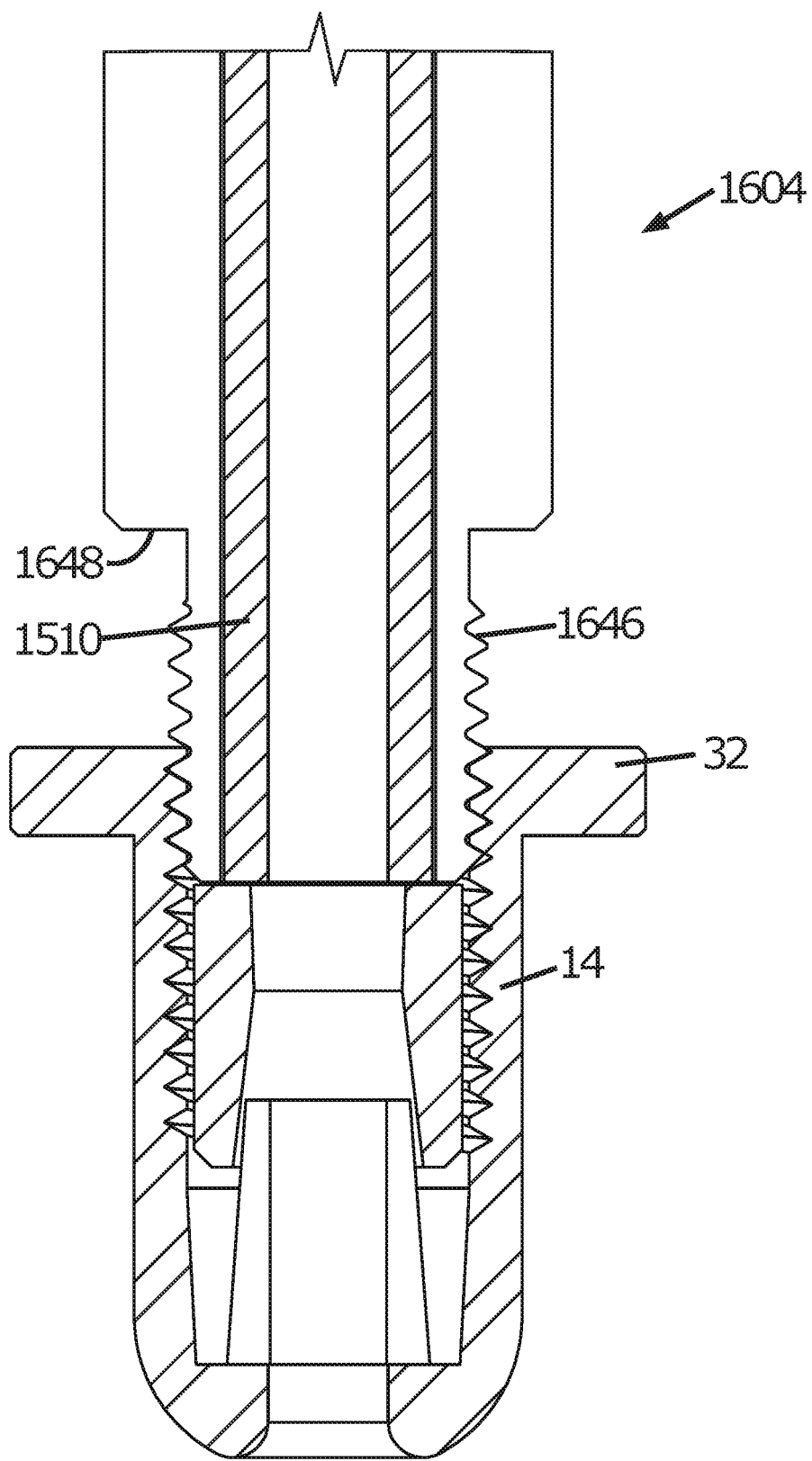
FIG. 59 is a schematic cross-sectional view of an alternative embodiment of an installation instrument stem.

FIG. 59 illustrates another alternative stem 1604. It includes male threads 1646 formed on a distal end which engage female threads formed on anchor housing 14. It also includes an axially-facing shoulder 1648. When fully threaded onto the stem 1604, the flange 32 of the housing 14 abuts the shoulder 1646. This construction provides a highly rigid interconnection between the housing 14 and the stem 1604 in order to maximize the surgeon's control and ability to manipulate the anchor 12. The hollow pushrod 1610 is mounted inside the stem and operates like the pushrod 1510 described above in order to swage the collet 16 when desired.

Figure 60:
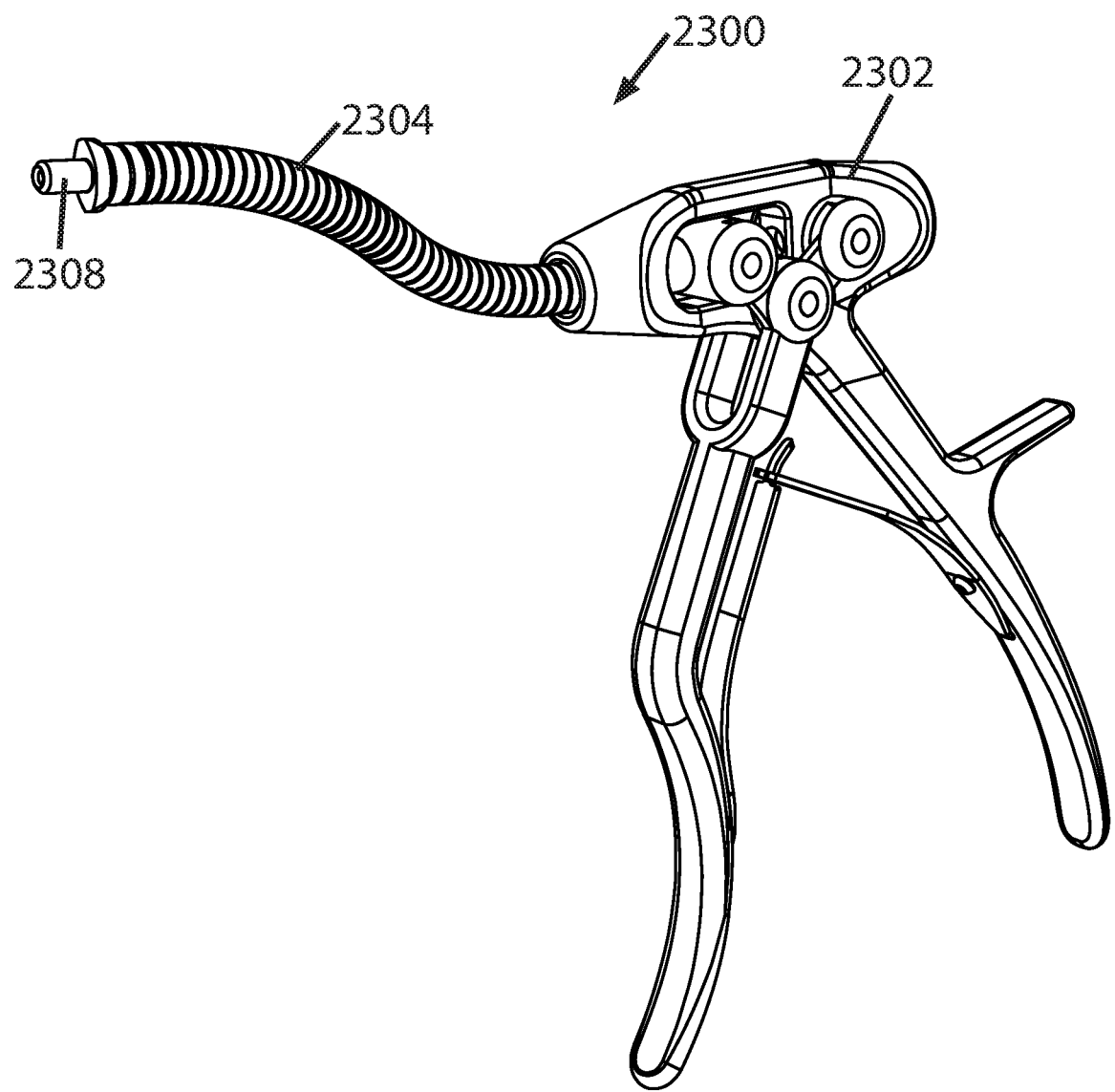
FIG. 60 is a schematic perspective view of an installation instrument having an alternative flexible stem.

FIG. 60 illustrates an alternative insertion instrument 2300. It includes a stem 2304 extending from the body 2302 and having an anchor connection mechanism 2308 disposed at a distal end thereof. The stem 2304 may be flexible as a result of its material selection. Alternatively, it may incorporate linked segments, corrugations, or similar structures to provide flexibility. A hollow pushrod (not visible), which may be flexible, extends through the interior of the stem 2304 and is slidably movable between retracted and extended positions. The hollow pushrod operates like the pushrod 1510 described above in order to swage the collet 16 when desired.

Figure 63:
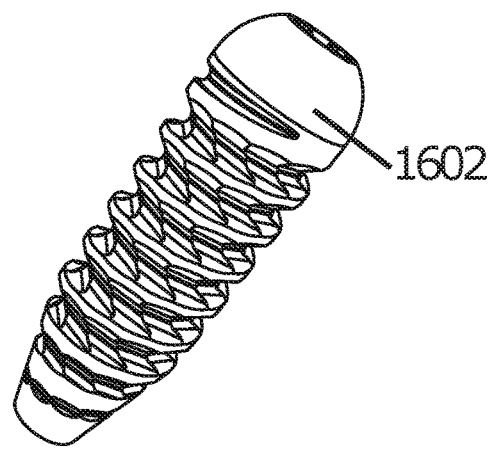
FIG. 63 is a schematic perspective view of a suture anchor.
Figure 64:
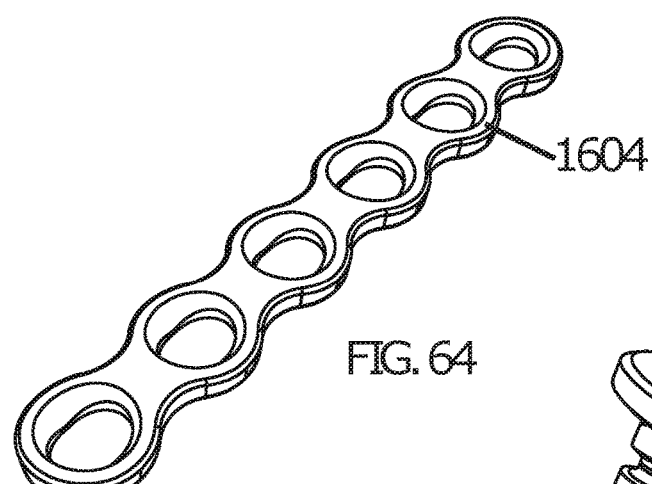
FIG. 64 is a schematic perspective view of an anchor plate.
Figure 65:
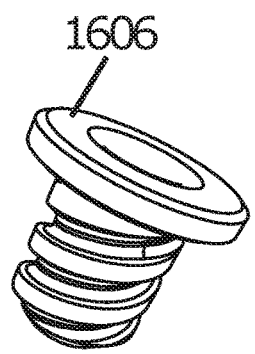
FIG. 65 is a schematic perspective view of a grommet.

Other anchoring devices may be used in conjunction with the various embodiments of anchors 12 described above in order to implant a tensile member 10. FIGS. 62-65 illustrate examples of various anchoring devices. 62 illustrates a "button" 1600 to which a tensile member may be tied. FIG. 63 illustrates a screw-in suture anchor 1602. FIG. 64 illustrates a plate 1604 having a series of openings formed therein, each of which may receive an anchor. FIG. 65 illustrates a grommet 1606 which has a smooth interior surface to allow a tensile member to pass freely therethrough.

Figure 66:
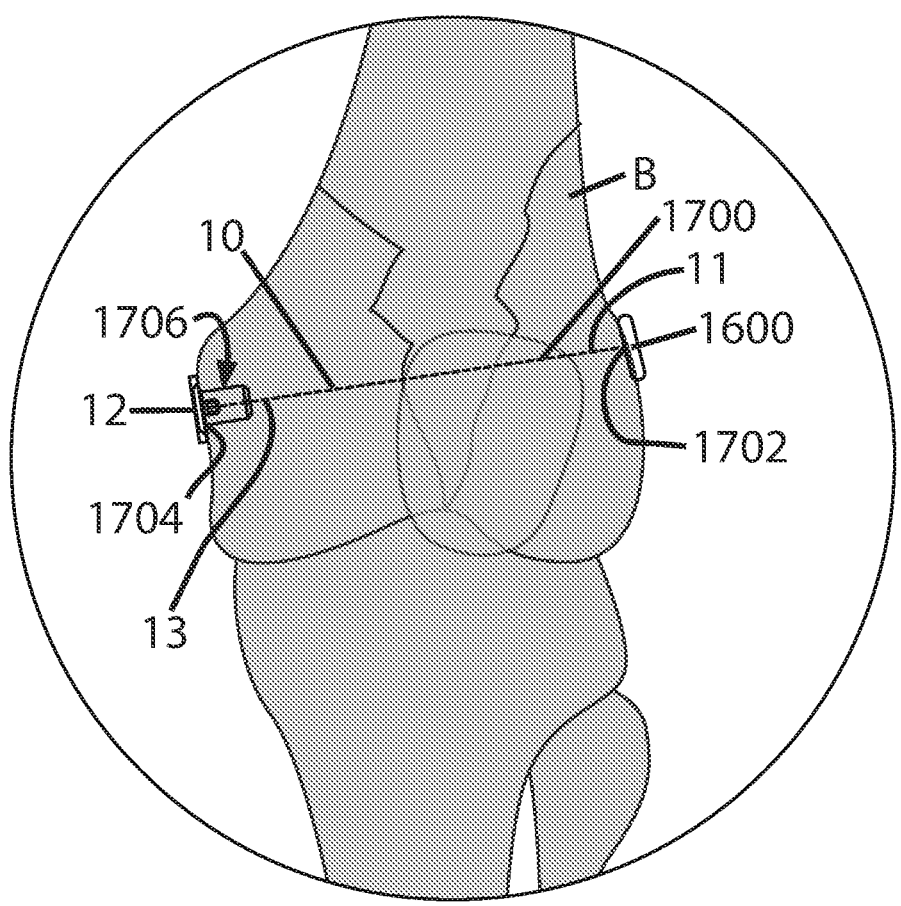
FIG. 66 is a schematic diagram of a tensile member implanted in a human femur.

The method of applying these principles for implantation and tensioning of a tensile member 10 will now be described in more detail with reference to FIGS. 2 and 66. This particular example illustrates the use of a tensile member 10 to stabilize a human femur. It will be understood that this is merely an example, and that the apparatus and methods described herein may be used to secure and tension a tensile member in any application.

Initially, a tensile member 10 is provided. An appropriate route through bone "B" or other tissue is determined, and a passage 1700 having first and second ends 1702, 1704 is drilled in the bone B. The second end 1704 of the passage 1700 is prepared to receive the anchor 12, for example by drilling an appropriately-sized bore 1706 communicating with the passage 1700.

A first end 11 of the tensile member 10 is secured in the first end of the passage 1700. This may be done using the anchor 12 as described above, or some other type of anchor. In the illustrated example, the first end 11 of the tensile member is secured to a button 1600 as described above. The tensile member 10 is threaded through the passage 1700 so that its second end 13 extends from the second end 1704 of the passage 1700.

An anchor 12 according to one of the embodiments described above is loaded into the installation instrument 1500 described above or another appropriate instrument. The second end 13 of the tensile member 10 is threaded through the anchor 12 and the installation instrument 1500 and optionally through the tensioner 1520.

The installation instrument 1500 is then used to seat to the anchor 12 into the bore 1706 formed in the bone B. The seating process may include methods such as simple axial driving, an adhesive bond, threading, screwing into the bone B with small screws through the flange, or counter-sinking into the bone surface.

With the anchor 12 seated, but the collet 16 not yet swaged, tension may be applied to the tensile member 10, for example using the tensioner 1520 described above. This is referred to as "provisional tensioning".

The properties of the anchor 12 and the installation instrument 1500 enables provisional and permanently stable tensioning of the tensile member 10, and allows the surgeon to load-cycle and re-tension the tensile member 10 before setting final tension. More specifically, With the insertion instrument 1500 abutted against the flange 32 of the anchor 12, tension can be added and removed. The ligament or joint being repaired can be load cycled by moving it through some or all of its range of motion before setting final tension.

In addition to producing more accurate and repeatable suture tensions, provisional tensioning with a load-setting/load-reading instrument (especially when the suture crosses the axis of a joint, such as a medial collateral ligament (MCL) repair technique) allows the surgeon to visualize the increase/decrease in tension throughout the joint range of motion (max flexion to max extension). This allows the surgeon to ensure that the tension stays within an acceptable range—and this check is done after load cycling the ligament in question to ensure the settle-in period is complete.

Once the surgeon is satisfied with the tension established, the insertion instrument 1500 may be activated. The driving mechanism 1512 is used to force the pushrod 1510 towards the actuated position. This drives the sleeve 18 down over the collet 16, thus swaging the collet 16 around the second end 13 of the tensile member 10. This swaging action takes place with the collet 16 bottomed out at the first end 22 of the housing 14 of the anchor 12. Accordingly, the act of swaging causes little to no change in the tension applied to the tensile member 10.

As the sleeve 18 reaches the fully-actuated position, the sleeve retention features of the housing 14 and the sleeve 18 become mutually engaged. FIG. 2 shows an example in which the locking tabs 66 of the housing 14 engage the annular step 90 of the sleeve 18. This prevents retraction of the sleeve 18 and sets the tensile member 10 permanently in position, with the predetermined amount of tension. The tensile member 10 is thus secured to the bone B with a desired tension.

Figure 61:
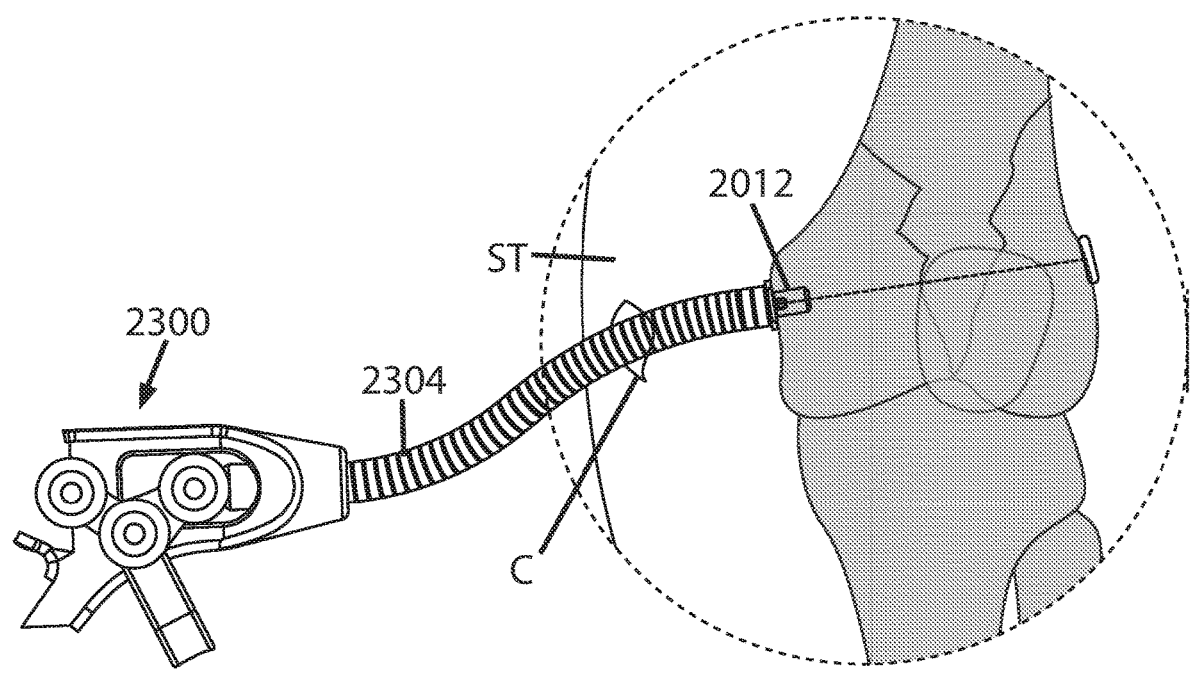
FIG. 61 is a schematic view showing the percutaneous and/or arthroscopic installation instrument of FIG. 60 being used implant an anchor in a human knee joint.
Figure 62:
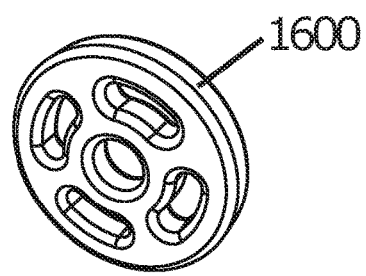
FIG. 62 is a schematic perspective view of a button anchor.

The procedure described above with reference to FIG. 66 may be performed as a conventional or "open" procedure or in an arthroscopic procedure. FIG. 61 illustrates how the alternative insertion instrument 2300 may further facilitate an arthroscopic procedure. The stem 2304 is shown as being flexed in a curved shape so that it can pass through a small closed incision "C" in the soft tissue "ST" surrounding the joint. The other steps in the procedure described above would be identical.

Figure 69:
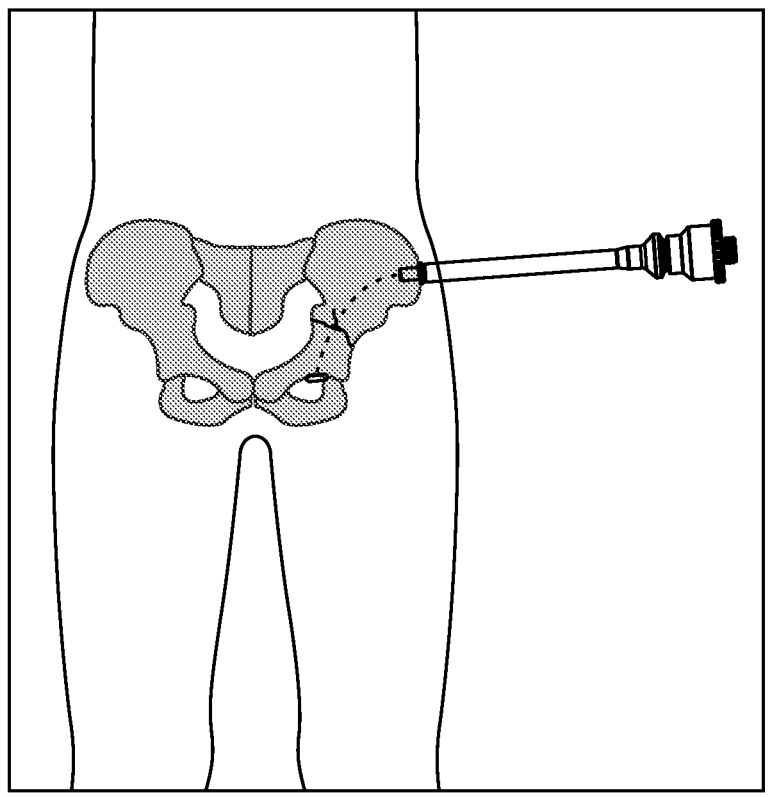
FIG. 69 is a schematic view showing an arthroscopic procedure in which a rigid stem is used to position an anchor in the pelvic region, close to the superficial surface of the skin.
Figure 70:
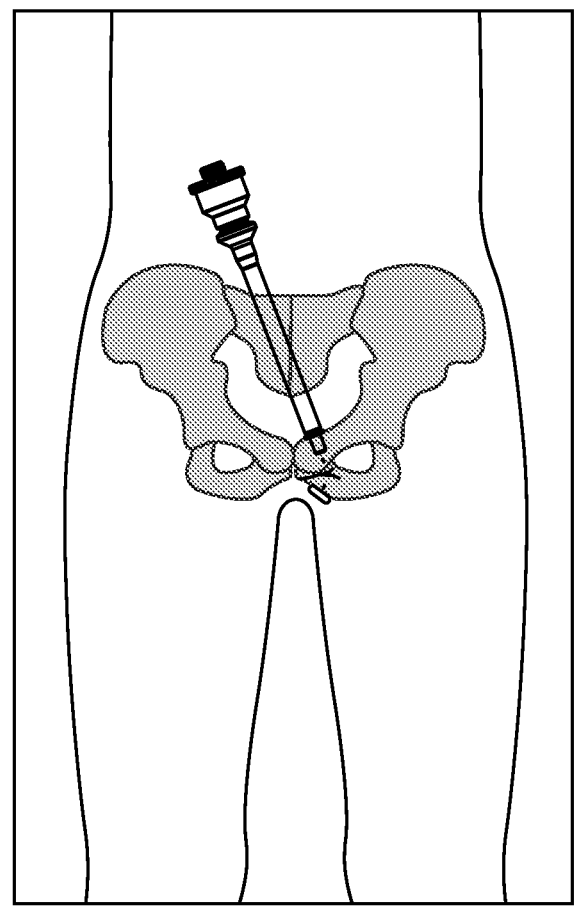
FIG. 70 is a schematic view showing an arthroscopic procedure in which a rigid stem is used to position an anchor in the pelvic region, far from the superficial surface of the skin.
Figure 71:
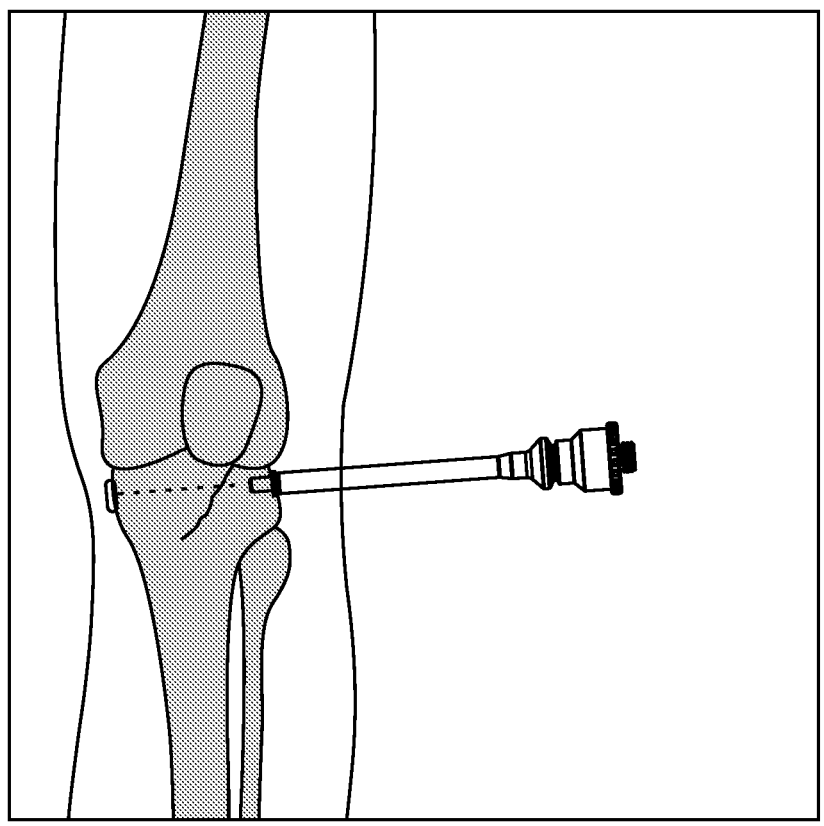
FIG. 71 illustrates an arthroscopic procedure in which a rigid stem is used to position an anchor in the knee region, close to the superficial surface of the skin.

FIG. 69 illustrates an arthroscopic procedure in which a rigid stem is used to position the anchor in the pelvic region, close to the superficial surface of the skin. 70 illustrates an arthroscopic procedure in which a rigid stem is used to position the anchor in the pelvic region, far from the superficial surface of the skin. 70 illustrates an arthroscopic procedure in which a rigid stem is used to position the anchor in the knee region, close to the superficial surface of the skin.

Figure 67:
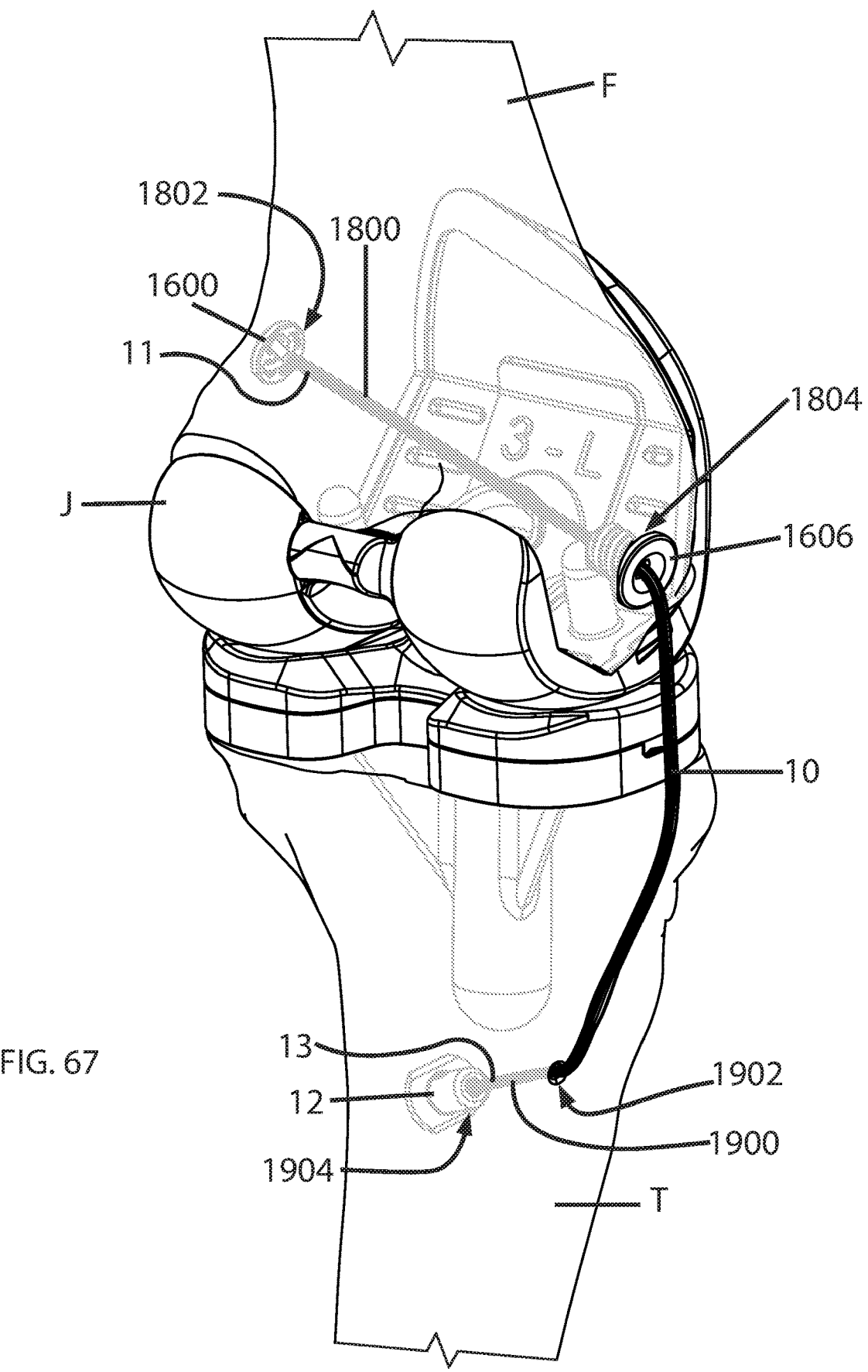
FIG. 67 is a schematic perspective view of a tensile member implanted in a human knee joint.

As noted above, apparatus and methods described above may be used to implant tensile members 10 for numerous different types of repairs and procedures. One specific example where the apparatus and methods are useful is to implant a tensile member in conjunction with a total knee replacement (TKR). This is referred to as a tension ligament augmentation (TLA) of the knee joint. FIG. 67 shows an example of a human knee joint comprising a portion of the "F" articulated with the tibia "T". The knee joint has implanted therein an artificial joint "J", the structure of which is outside the scope of the present invention.

A first passage 1800 having first and second ends 1802, 1804 extends through the femur F. A second passage 1900 having first and second ends 1902, 1904 extends through the tibia T. The second end 1904 of the second passage 1900 is prepared to receive the anchor 12.

A first end 11 of the tensile member 10 is secured in the first end 1802 of the first passage 1800 by an anchoring element such as a button 1600. A grommet 1606 is secured in the second end 1804 of the first passage 1800, and the tensile member 10 passes through the grommet 1606.

The tensile member 10 further extends around the lateral aspect of the knee joint J down along the upper portion of the tibia T and into the first end 1902 of the second passage 1900. The second end 13 of the tensile member 10 extends through the second passage, exiting at the second and 1904 of the second passage 1900.

An anchor 12 is described above is implanted in the second in 1902 of the second passage 1900. The second end 13 of the tensile member 10 extends through the anchor 12. The anchor 12 may be installed, and the tensile member 10 may be tensioned and swaged in place using the insertion tool 1500 and methods substantially as described above.

The apparatus and method described herein has numerous benefits compared to the prior art. It provides a modular device and implant system and method that enables provisional and permanently stable tensioning of the tensile member, with minimally-invasive access to and limited visualization of the bone surface, using a device that is small and low-profile to prevent stress-shielding and soft tissue hang-up, implanted by simple and intuitive instrumentation that optimizes workflow and can be accomplished by one person.

The device and method described above may be used for procedures such as tensioning ligaments and tendons, augmenting ligaments and tendons, repairing and/or replacing ligaments and tendons, and reducing and fixate bone fractures.

The foregoing has described apparatus and methods for medical implants. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. An apparatus for anchoring a tensile member to bone, comprising:
   an anchor, comprising:
      a housing extending along a central axis between open first and second ends, and having a hollow interior;
      a collet disposed in the hollow interior of the housing, the collet having a peripheral wall defining a central bore for accepting a tensile member therethrough and an exterior surface, wherein the collet is configured to be swaged around and against the tensile member;
      a sleeve having a peripheral wall defining opposed interior and exterior surfaces, the sleeve disposed in the hollow interior of the housing and positioned generally axially adjacent to the collet, so as to be movable parallel to the central axis between first and second positions; and
      wherein at least one of the exterior surface of the collet and the interior surface of the sleeve is tapered and the sleeve and the collet are arranged such that movement of the sleeve from the first position to the second position will cause the interior surface of the sleeve to bear against the exterior surface of the collet, causing the collet to swage radially inwards around and against the tensile member without moving axially relative to the housing or tensile member; and
   an insertion instrument including:
      a stem having an anchor connection mechanism;
      a hollow pushrod extending through the stem and slidably movable between retracted and extended positions; and
      a driving mechanism operable to move the pushrod between the retracted and extended positions.

2. The apparatus of claim 1, wherein the housing comprises a body and a flange extending radially outward from the body at the second end of the housing.

3. The apparatus of claim 2, wherein the flange includes chamfered surfaces which are configured to engage jaws of an insertion instrument.

4. The apparatus of claim 2, wherein the housing is generally cylindrical in shape, the body has an outer diameter of about 3 to 12 mm, and the flange has an outer diameter of about 5 to 20 mm.

5. The apparatus of claim 1, wherein the housing includes an internal flange disposed at the first end configured to block axial movement of the collet in one direction.

6. The apparatus of claim 5, wherein the collet and the internal flange of the housing are further configured such that axial movement of the collet towards the first end of the housing will cause the internal flange to bear against the exterior surface of the collet, causing the collet to swage radially inwards around and against the tensile member.

7. The apparatus of claim 5, wherein the housing includes a transition section axially adjacent the internal flange configured to apply a radially inward force against the collet.

8. The apparatus of claim 1, further comprising engagement means formed on the housing for connecting the housing to an insertion instrument.

9. The apparatus of claim 1 wherein the housing and the collet comprise one monolithic member.

10. The apparatus of claim 1 wherein the housing, the collet, and the sleeve comprise one monolithic member.

11. The apparatus of claim 1 wherein the sleeve and the housing each include retention elements, the retention elements collectively configured to permit movement of the sleeve from the first position to the second position and to mutually engage each other so as to prevent the sleeve from moving out of the second position.

12. The apparatus of claim 11 when the retention elements comprise predetermined dimensions of the sleeve and the housing effective to permit radial clearance between the sleeve and the housing in the first position and to define a radial interference between the sleeve and the housing and the second position.

13. The apparatus of claim 11 wherein the retention elements comprise locking tabs disposed on one of the housing and the sleeve, and an annular step disposed on the other of the housing and of the sleeve.

14. The apparatus of claim 1 wherein the collet is made from a material which has a lower effective elastic modulus than a material of the sleeve.

15. The apparatus of claim 14 wherein the collet is made from sintered material.

16. The apparatus of claim 1 wherein the collet incorporates areas of removed material so as to facilitate collapse of the collet.

17. The apparatus of claim 1 wherein the collet incorporates a shape on the first end so as to facilitate collapse of the collet.

18. The apparatus of claim 1 wherein the stem is flexible.

19. The apparatus of claim 1, wherein the anchor connection mechanism comprises opposed jaws movable between open and closed positions in response to movement of the pushrod, the jaws being shaped to engage the anchor in the closed position.

20. The apparatus of claim 19, further comprising a generally U-shaped clip disposed between the jaws and axially movable between a first position which is free of the jaws and a second position which retains the jaws in the closed position.

21. The apparatus of claim 19, further comprising a lock sleeve disposed on the outside of the jaws and axially moveable between a first position which is free of the jaws and a second position which retains the jaws in the closed position.

22. The apparatus of claim 1 wherein the anchor connection mechanism is configured to be detached from the housing of the anchor without putting torsional force on the housing.

23. The apparatus of claim 1 wherein the anchor connection mechanism is a breakaway connection between the stem and the housing.

* * * * *